(12) United States Patent  
Collier et al.

(10) Patent No.: US 9,207,246 B2
(45) Date of Patent: Dec. 8, 2015

(54) METHOD AND DEVICE FOR IMMUNOASSAY USING NUCLEOTIDE CONJUGATES

(71) Applicant: Abbott Point of Care Inc., Princeton, NJ (US)

(72) Inventors: G. Bruce Collier, Fitzroy Harbour (CA); Cary James Miller, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 258 days.

(21) Appl. No.: 13/865,425

(22) Filed: Apr. 18, 2013

(65) Prior Publication Data

US 2013/0230854 A1 Sep. 5, 2013

Related U.S. Application Data

(62) Division of application No. 12/650,241, filed on Dec. 30, 2009, now Pat. No. 8,445,199.

(60) Provisional application No. 61/142,048, filed on Dec. 31, 2008.

(51) Int. Cl.
  *G01N 33/68* (2006.01)
  *G01N 33/58* (2006.01)
  *G01N 33/53* (2006.01)

(52) U.S. Cl.
  CPC ........ *G01N 33/6887* (2013.01); *G01N 33/5302* (2013.01); *G01N 33/58* (2013.01); *G01N 2458/10* (2013.01)

(58) Field of Classification Search
  CPC G01N 33/6887; G01N 33/58; G01N 33/5302
  See application file for complete search history.

(56) References Cited

U.S. PATENT DOCUMENTS

| 5,096,669 | A | 3/1992 | Lauks et al. |
| 5,164,311 | A | 11/1992 | Gupta |
| 5,416,026 | A | 5/1995 | Davis |
| 5,447,440 | A | 9/1995 | Davis et al. |
| 5,514,253 | A | 5/1996 | Davis et al. |
| 5,593,639 | A | 1/1997 | Makino et al. |

(Continued)

FOREIGN PATENT DOCUMENTS

| JP | H10-508741 | 1/1996 |
| JP | 2001-503517 | 3/2001 |

(Continued)

OTHER PUBLICATIONS

Non-Final Office Action for U.S. Appl. No. 12/650,241 dated May 2, 2012.

(Continued)

*Primary Examiner* — Melanie Y Brown

(57) ABSTRACT

A composition of matter for use in an immunoassay devices and method comprising a signal antibody, e.g., FAB fragment, covalently linked to a first nucleotide; and one or more signal elements, e.g., signal enzymes such as ALP or fluorescent dyes, each covalently linked to a second nucleotide, wherein the first nucleotide has one or more repeated sequences, and the second nucleotide is bound to one of the one or more repeated sequences on said first nucleotide, and wherein the ratio of the signal antibody to the signal element is controlled by the number of repeated sequences.

6 Claims, 24 Drawing Sheets

(56) References Cited

U.S. PATENT DOCUMENTS

| | | | |
|---|---|---|---|
| 5,605,664 | A | 2/1997 | Lauks et al. |
| 5,609,824 | A | 3/1997 | Lauks et al. |
| 5,614,416 | A | 3/1997 | Lauks et al. |
| 5,628,961 | A | 5/1997 | Davis et al. |
| 5,635,602 | A | 6/1997 | Cantor et al. |
| 5,656,493 | A | 8/1997 | Mullis et al. |
| 5,789,253 | A | 8/1998 | Lauks et al. |
| 6,030,827 | A | 2/2000 | Davis et al. |
| 6,110,687 | A | 8/2000 | Nilsen |
| 6,355,418 | B1 | 3/2002 | Schmidt |
| 6,379,883 | B2 | 4/2002 | Davis et al. |
| 7,419,821 | B2 | 9/2008 | Davis et al. |
| 7,473,767 | B2 | 1/2009 | Dimitrov |
| 2002/0077468 | A1 | 6/2002 | Lovenberg et al. |
| 2003/0170881 | A1 | 9/2003 | Davis et al. |
| 2003/0207295 | A1 | 11/2003 | Gunderson et al. |
| 2004/0002095 | A1 | 1/2004 | Liu et al. |
| 2004/0018577 | A1 | 1/2004 | Emerson et al. |
| 2005/0019842 | A1 | 1/2005 | Prober et al. |
| 2005/0054078 | A1 | 3/2005 | Miller et al. |
| 2005/0095627 | A1 | 5/2005 | Kolman et al. |
| 2006/0160164 | A1 | 7/2006 | Miller et al. |
| 2007/0154922 | A1 | 7/2007 | Collier et al. |
| 2010/0081216 | A1 | 4/2010 | Yager et al. |
| 2010/0291562 | A1 | 11/2010 | Adler |

FOREIGN PATENT DOCUMENTS

| | | |
|---|---|---|
| JP | 2002-209594 | 7/2002 |
| JP | 2005-519304 | 6/2005 |
| JP | 2005-524403 | 8/2005 |
| JP | 2005-534006 | 11/2005 |
| JP | 2005-534907 | 11/2005 |
| JP | 2006-501808 | 1/2006 |
| JP | 2008-545142 | 12/2008 |
| WO | WO 96/00795 | 1/1996 |
| WO | WO 01/36666 | 5/2001 |
| WO | WO 01/59425 | 8/2001 |
| WO | WO 2006/071770 | 7/2006 |

OTHER PUBLICATIONS

Final Office Action for U.S. Appl. No. 12/650,241 dated Oct. 11, 2012.

Notice of Allowance for U.S. Appl. No. 12/650,241 dated Jan. 25, 2013.

International Search Report and Written Opinion for PCT/US2009/069846 mailed Mar. 5, 2010.

Adler, et al., (2008), Sensitivity by combination: immune-PCR and related technologies. Analyst, 133, 702-718.

Apple, et al. (2008). Use of Centaur TnI-Ultra Assay for Detection of Myocardial Infarction and Adverse Events in Patients with Symptoms Suggestive of Acute Coronary Syndrome. Clinical Chemistry, 54(4), 723-728.

Cook, et al. (1995). Photochemically Initiated protein splicing. Angewandte Chemie International Edition in English, 34(15), 1629-1630.

Duckworth, et al. (2007). A Universal Method for the Preparation of Covalent Protein-DNA Conjugates for use in Creating Protein Nanostructures. Angew. Chem. Int. Ed., 46, 8819-8822.

Fan et al. (2008). Integrated Barcode Chips for Rapid, Multiplexed Analysis of Protein in Microliter Quantities of Blood. Nature Biotechnology, 26, 1373-1378.

Heyduk, et al. (2008). Molecular Pincers: Antibody-Based Homogeneous Protein Sensors. Analytical Chemistry, 80(13), 1552-5159.

Jung et al. (2008). Recent Advances in immobilization methods of antibodies on solid supports. Analyst, 133, 697-701.

Kawabata et al. (2005). Liquid-Phase Binding Assay of alpha-Fetoprotein Using DNA-Coupled Antibody and Capillary Chip Electrophoresis. Analytical Chemistry, 77(17), 5579-5582.

Ketomaki et al. (2006). A Mixed-Phase Immunoassay Based on Simultaneous Binding of Fluorescently Tagged and PNA-Conjugated peptide Epitopes on Anitbodies: Quantification on PNA-Coated Microparticles. Bioconjugate Chemistry, 17(4), 1063-1068.

Kozlov et al. (2004). Efficient strategies for the conjugation of oligonucleotides to antibodies enabling highly sensitive protein detection. Biopolymers, 73(5), 621-630.

Kuijpers et al. (1993). Specific Recognition of Antibody-Oligonucleotide Conjugates by Radiolabeled Antisense Nucleotides: A Novel Approach for Two-Step Radioimmunotherapy of Cancer. Bioconjugate Chemistry, 4(1), 94-102.

Lequin (2005). Enzyme Immunoassay (EIA)/Enzyme-Linked Immunosorbent Assay (ELISA). Clinical Chemistry, 51(12), 2415-2418.

Lovrinovic et al. (2003). Synthesis of protein-nucleic acid conjugates by expressed protein ligation. Chemical Communications, 7, 822-823.

Niemeyer et al. (1994). Oligonucleotide-directed self-assembly of proteins: semi-synthetic DNA-streptavidin hybrid molecules as connectors for the generation of macroscopic arrays and the construction of supramolecular bioconjugates. Nucleic Acids Research, 22(25), 5530-5539.

Niemeyer et al. (1998). Covalent DNA-Streptavidin Conjugates as Building Blocks for novel Biometallic Nanostructures. Angew. Chem. Int. Ed., 37(16), 2265-2268.

Niemeyer et al. (2001). Nanostructured DNA-Protein Aggregates Consisting of Covalent Oligonucleotide-Streptavidin Conjugates. Bioconjugate Chemistry, 12(3), 364-371.

Niemeyer et al. (2002). DNA-directed Assembly of Bienzymic complexes from in Vivo Biotinylated NAD(P)H:FMN Oxidoreductase and Luciferase. ChemBioChem, 3(2-3), 242-245.

Niemeyer et al. (2005). Immuno-PCR: high sensitivity detection of proteins by nucleic acid amplification. Trends in Biotechnology, 23(4), 208-216.

Niemeyer et al. (2000). Self-assembled nanostructures based on DNA: towards the development of nanobiotechnology. Current Opinion in Chemical Biology, 4(6), 609-618.

Reyes et al. (1993). Preparation of pure oligonucleotide-alkaline phosphatase conjugates. Nucleic Acids Research, 21(23), 5532-5533.

Sano et al. (2000). Immuno-PCR: very sensitive antigen detection by means of specific antibody-DNA conjugates. Science, 258(5079), 120-122.

Seeman (1999). DNA engineering and its application to nanotechnology. Trends in Biotechnology, 17(11), 437-443.

Storhoff et al. (1999). Programmed materials synthesis with DNA. Chemical Review, 99(7), 1849-1862.

Takeda et al. (2008). Covalent split protein fragment-DNA hybrids generated through N-terminus-specific modification of proteins by oligonucleotides. Organic and Biomolecular Chemistry, 6, 2187-2194.

Tennila et al. (2008). Peptide-oligonucleotide conjugates form stable and selective complexes with Antibody and DNA. Bioconjugate Chemistry, 19(7), 1361-1367.

Tomkins et al. (2001). Preparation of Symmetrical and Unsymmetrical DNA-Protein Conjugates with DNA as a molecular Scaffold. ChemBioChem, 2(5), 375-378.

Wacker et al. (2004). Performance of antibody microarrays fabricated by either DNA-directed immobilization, direct spotting, or streptavidin-biotin attachment: A comparative study. Analytical Biochemistry, 330(2), 281-287.

Zethelius et al. (2006). Troponin I as a Predictor of Coronary Heart Disease and Mortality in 70-year-old men: A community-based cohort study. Circulation, 113, 1071-1078.

Zhang et al. (2007). Multiple labeling of Antibodies with Dye/DNA Conjugate for Sensitivity Improvement in Fluorescence Immunoassay. Bioconjugate Chemistry, 18(5), 1668-1672.

Zhu et al. (2008). Part-per-trillion level detection of estradiol by competitive fluorescence immunoassay using DNA/dye conjugate as antibody multiple labels. Analytica Chimica Acta, 624(1), 141-146.

Office Action for European Appl. No. 09797246.7 dated Oct. 6, 2014.

Brune, et al., 1993, Proceedings of the National Academy of Sciences, vol. 90, 3835-3839.

(56) References Cited

OTHER PUBLICATIONS

Hanahan et al., 1991, "Plasmid Transformation of *Escherichia coli* and other bacteria", Methods of Enzymology, vol. 204: 63-113.
Birnboim et al., 1979, Nucleic Acids Research, vol. 7 (6): 1513-1523.
International Preliminary Report on Patentability for PCT/US2009/069846 mailed Jul. 14, 2011.
Office Action for European Appl. No. 09797246.7 dated Mar. 26, 2014.
Office Action for corresponding Chinese Appl. No. 200980153231.3 dated Dec. 6, 2013.
Office Action for corresponding Japanese Appl. No. 2011-543729 dated Nov. 15, 2012.
Office Action for corresponding Australian Appl. No. 2009334505 dated Jul. 17, 2012.

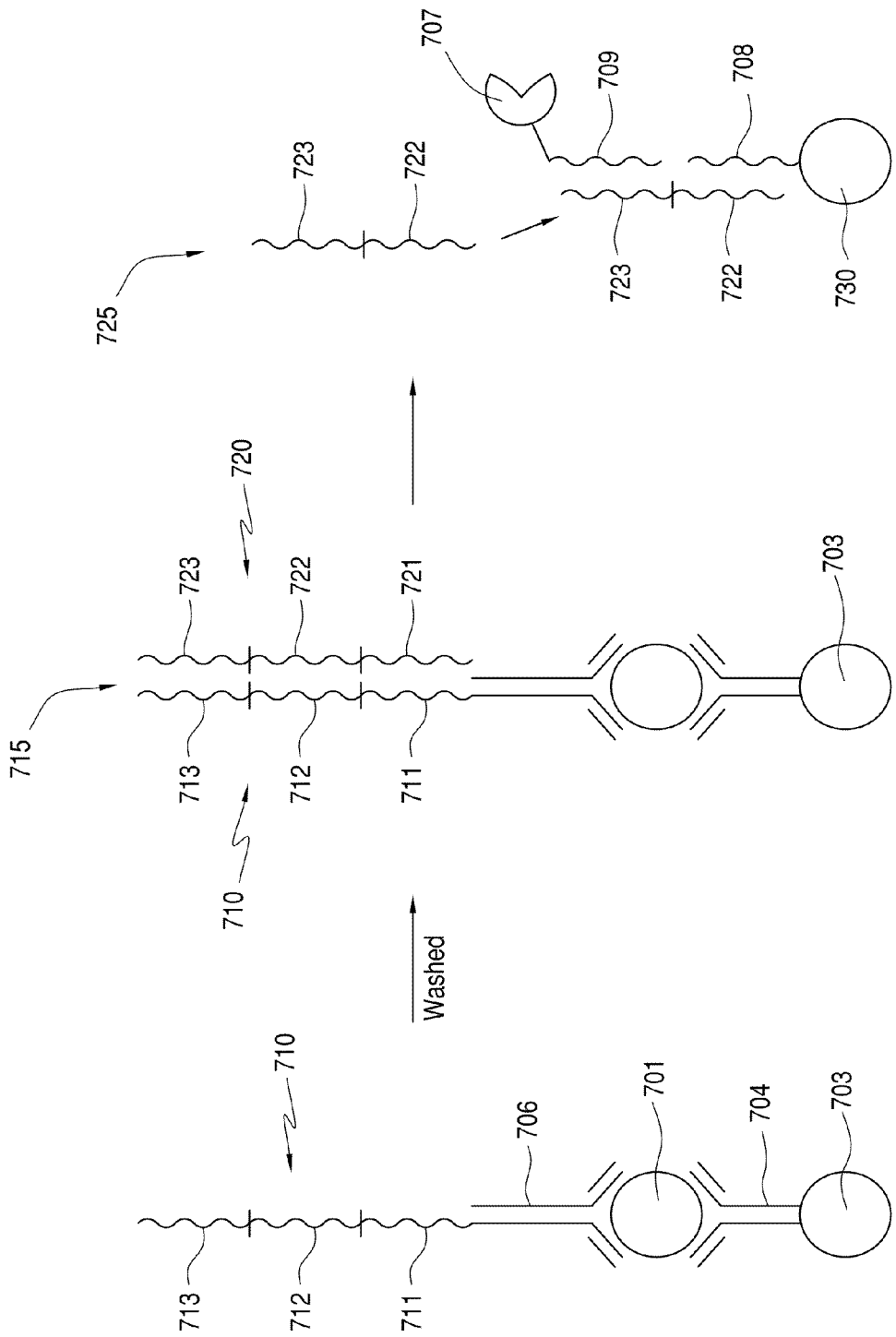

Fluorescing fractions from size exclusion column

S300 column fractions from ALP LC-SPDP reaction

S300 column fractions from ALP LC-SPDP reacted with DTT-treated synthetic oligonucleotide Chronoamperometric plot of three dilutions ($10^{-1}$(37.3 ng), $10^{-2}$(3.73 ng), $10^{-3}$ (0.37 ng) of ALP-A' conjugate tested in 'A' containing i-STAT 'immuno' cartridges using WinISD software developed by Bill Keogh S300 Column fractions from PEP-3 F(ab')2 reacted with LC-SPDP

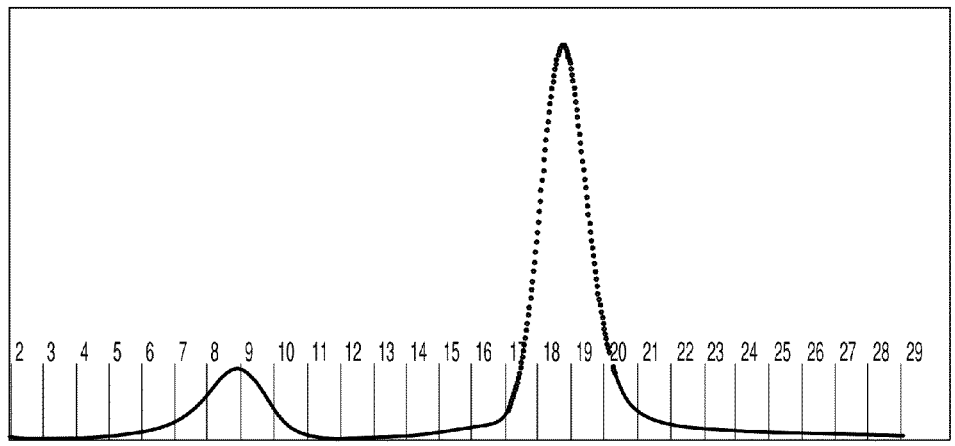

S300 columns fractions from PEP-3 F(ab')2 LC-SPDP reacted with DTT treated a synthetic oligonucleotide

FIG. 28

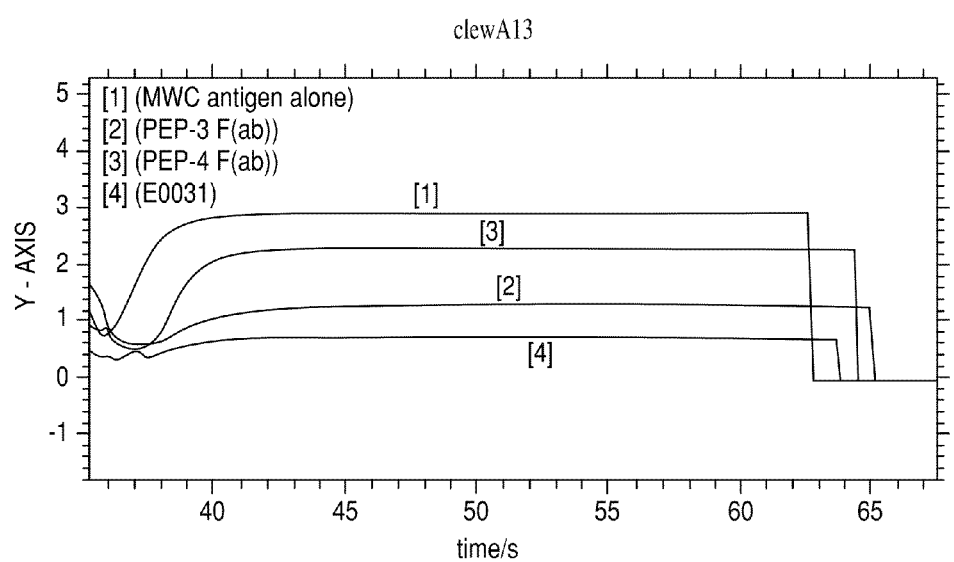

Chronoamperometric plot of production version of cTnI cartridge using antigen competition from addition of free antibody or conjugate to the sample used. [1] MWC 92353 diluted to 2.59 ng/ml and used 2 uL [5.2 pg]. [2] Antigen with addition of 49.2 ng PEP-3 F(ab), [3] Antigen with addition of 61.8 ng PEP-4 F(ab), [4] Antigen with addition of 109 ng E0031 conjugate

FIG. 29

Chronoamperometric results from i-STAT immuno-cartridge with cTnI capture beads and no conjugate, spiked with E0030 [747 ng] = E0031 [218 ng] with [2] antigen and without [1] MWC antigen

METHOD AND DEVICE FOR IMMUNOASSAY USING NUCLEOTIDE CONJUGATES

CROSS REFERENCE TO RELATED APPLICATION(S)

This application is a divisional of U.S. application Ser. No. 12/650,241, filed Dec. 30, 2009, which claims priority to U.S. Provisional Application No. 61/142,048, filed Dec. 31, 2008, which are incorporated herein by reference in their entireties.

SEQUENCE LISTING

This application contains a Sequence Listing which has been submitted in ASCII format via EFS-Web and is hereby incorporated by reference in its entirety. Said ASCII copy, created on Apr. 18, 2013, is named 2013-04-18-215105-02651_ST25.txt and is 2,368 bytes in size.

BACKGROUND OF THE INVENTION

1. Field of the Invention

This invention relates to methods and devices for conducting a variety of assays for determining the presence of an analyte in samples using nucleotide conjugates.

2. Discussion of the Background Information

The detection of some target analytes in low concentrations is important for the early diagnosis of some illnesses. For example, recent research suggests that measuring cardiac Troponin I (cTnI) at levels below those of typical commercial assays provides information of value to clinicians. Note that even very low levels of cTnI, i.e., below those considered indicative of acute myocardial infarction, may be indicative of future adverse cardiovascular status. For example, Zethelius et al., (2006, "Troponin I as a predictor of Coronary Heart Disease and Mortality in 70-year-old men: A community-based cohort study", *Circulation*, vol. 113:1071-1078) performed a study to investigate the correlation between cardiac TnI concentrations and the prediction of future coronary heart disease. They observed that in 70 year old men that showed no clinical signs of cardiovascular disease, but exhibited slightly elevated levels of cardiac TnI could predict a forthcoming coronary heart disease event. Furthermore, Apple et al., (2008, "Use of the Centaur TnI-Ultra Assay for Detection of Myocardial Infarction and Adverse Events in Patients Presenting With Symptoms Suggestive of Acute Coronary Syndrome", Clinical Chemistry, vol. 54(4):723-728) performed a study in a sensitive troponin assay to assess the prognostic value of assessing the risk of short-term adverse events based on cTnI values at the limit of detection and 99th percentile reference value. They concluded that "our data add to the growing evidence that with improved, analytically robust cTn assays with low LoDs [levels of detection], any measurable cTnI implies a higher risk than cTnI concentrations below an assay's Loa."

Current point-of-care immunoassay technology, although highly valuable in its ability to measure the presence and concentration of various target analytes, is somewhat limited in its ability to reliably detect very low levels of target analytes such as cTnI. Thus, the need exists for reliably detecting low levels of target analytes such as cTnI, particularly in point-of-care immunoassay analyte detecting devices.

U.S. Pat. No. 7,419,821, the entirety of which is incorporated herein by reference, utilizes a sandwich assay where two capture antibodies are immobilized on an electrode and two signal antibodies, e.g., FAB (Fragment Antigen Binding) antibody fragments, are labeled with an signal enzyme, such as alkaline phosphatase (ALP), to form a signal conjugate. An analyte, e.g., antigen such as cTnI, binds to the capture antibodies and the signal antibodies to form a sandwich assay, which provides a signal indicating the presence of the analyte. Conventionally, signal antibodies are bound to signal enzymes to form the signal conjugates through cross-linking technologies. These synthesis conditions lead to a wide range in the ratio of signal antibodies to label enzymes as well as in the number of signal enzymes per signal conjugate and in the number of signal antibodies per conjugate. For FAB antibody fragments, for example, there typically is a statistical population of signal conjugates having from no (0) FAB to an estimated 15 FAB per signal conjugate. As a result, the synthesized signal conjugates are typically purified by size exclusion chromatography to create a signal conjugate population having a narrower range of signal antibodies, e.g., FAB molecules, per signal conjugate. Such purification techniques, however, undesirably lead to reduced predictability and variable ratios of (i) signal antibodies to signal enzyme (e.g., FAB to ALP); (ii) signal enzyme to the signal conjugate, and (iii) signal antibody to signal conjugate. These variable ratios limit the ability of sandwich assays to reliably detect very low levels of target analytes in samples.

Enzyme-Linked Immunosorbent Assay (ELISA) based assays, used to assess the concentration of an analyte, e.g., antigen molecule in samples, including bodily fluids and environmental samples, conventionally require the ability to covalently link a signal antibody to an signal enzyme to generate the detection component of the assay. A history and review of this technology can be found in Lequin (2005, Enzyme Immunoassay (EIA)/Enzyme-Linked Immunosorbent Assay (ELISA), *Clinical Chemistry*, vol 51(12): 2415-2418). The need exists for increasing the sensitivity of ELISA assays as some antigens are present at extremely low concentrations.

U.S. Pat. No. 5,164,311 discloses an antibody-enzyme conjugate produced by adding sulfhydryl groups to an antibody and maleimidyl groups to an enzyme to produce a modified antibody and enzyme, and reacting the modified antibody and enzyme to produce the conjugate. In doing so, the '311 patent states that: "It would be advantageous to provide a labeling system wherein direct antibody-enzyme conjugates could achieve high enzyme-to-antibody ratios and therefore provide a higher degree of sensitivity approaching or equal to the avidin-biotin labeling system. Such an improved direct antibody-enzyme conjugate would not require the additional incubation step and washing steps as the biotin-avidin labeling system requires." The '311 patent describes the use of cross-linking agents such as SPDP with crosslinking molecules with the ability to crosslink sulfhydryl and maleimide groups for enzyme-antibody conjugates, however it is silent on using this for synthetic oligonucleotides.

Synthesis of conjugates based on enzymes and synthetic oligonucleotides have been developed for the molecular biology application of DNA hybridization techniques like Southern hybridization (Reyes & Cockerell, 1993, "Preparation of pure oligonucleotide-alkaline phosphatase conjugates", Nucleic Acids Research, vol 21(23): 5532-5533). The application of these conjugates does not anticipate their use for ELISA based assays.

With the development of an extremely sensitive DNA amplification strategy, e.g. Polymerase Chain Reaction (PCR) covered by U.S. Pat. No. 5,656,493 and others, it has been recognized that the combination of ELISA and PCR could increase detection sensitivity. For example, Sano et al., (2000, "Immuno-PCR: very sensitive antigen detection by means of specific antibody-DNA conjugates, Science, vol. 258(5079): 120-122) describe one of the earliest applications of this strategy to antigen detection. There are many references to the application of this approach including Kozlov et al., (2004, "Efficient strategies for the conjugation of oligonucleotides to Antibodies Enabling Highly Sensitive Protein Detection", Biopolymers, vol 73: 621-630) who describe synthetic oligonucleotide antibody conjugation synthesis strategies along with application of these specific conjugates for highly sensitive detection. This approach differs from the present invention as the synthetic oligonucleotide is used for subsequent DNA amplification, which is used as the sensitive detection approach.

The use of DNA amplification such as PCR is limited in that it does not permit the use of the synthetic oligonucleotide-antibody conjugate to be used in existing ELISA systems, and it also requires the use of thermal cycling capabilities requiring a dedicated device. Adler describes a related PCR approach to immunoassays in WO2008/122310. A number of related strategies have been reviewed by Adler et al., (2008, "Sensitivity by combination: immuno-PCR and related technologies", Analyst, vol. 133: 702-718); and Niemeyer et al., (2005, "Immuno-PCR: high sensitivity detection of proteins by nucleic acid amplification", Trends in Biotechnology, vol. 23(4): 208-216).

Cantor and Chuck (U.S. Pat. No. 5,635,602) describe a bis-protein conjugate using avidin/streptavidin binding linkage which they teach for immunoassays and PCR assays. For example, a first antibody is attached by a disulphide bond to DNA and the complimentary DNA at the other end is labeled with biotin. The biotin can bind to streptavidin which also binds biotinylated horseradish peroxidase (HRP). The latter can react with a substrate to generate a chemiluminescent signal. This disclosure differs as it does not teach the use of biotin-streptavidin moieties which do not permit the high degree of control compared to the multivalent streptavidin molecule.

Tennila et al., (2008, "Peptide-oligonucleotide conjugates form stable and selective complexes with Antibody and DNA", Bioconjugate Chemistry, vol. 19(7): 1361-1367) describe a short oligopeptide conjugated to a synthetic oligonucleotide used for antibody epitope mapping. They are silent on the ELISA assay.

Ketomaki & Lonnberg, 2006, ("A Mixed-Phase Immunoassay Based on Simultaneous Binding of Fluorescently Tagged and PNA-Conjugated peptide Epitopes on Antibodies: Quantification on PNA-Coated Microparticles, Bioconjugate Chemistry, vol. 17:1063-68.) describes a system where a complete antibody (with 2 F(ab) binding moieties) wherein one F(ab) binding moiety binds to a peptide with a fluorescent tag, and the other F(ab) binding moiety binds to a peptide sequence with a nucleic acid sequence (PNA). The PNA binds to the complementary PNA on a microparticle. These authors do not describe using covalent attachment of either the enzyme or the antibody, but rather the use of non-covalent binding of the antibody to a molecule that binds to the microparticle. Another non-covalent binding process is used for the antibody which generates a signal.

Wacker et al., (2004, "Performance of antibody microarrays fabricated by either DNA-directed immobilization, direct spotting, or streptavidin-biotin attachment: a comparative study", Analytical Biochemistry, vol. 330:281-287) describe the use of synthetic oligonucleotides covalently attached to capture antibody to generate antibody arrays, which they define as DNA-directed Immobilization (DDI). Another application for synthetic oligonucleotide-antibody conjugates is to immobilize capture antibodies onto solid supports (Jung et al., 2008, "Recent Advances in immobilization methods of antibodies on solid supports", Analyst, vol. 133: 697-701). This application differs from the present approach in that it does not teach immobilization of antibodies to solid supports. Lovrinovic et al., (2002, "Synthesis of protein-nucleic conjugates by expressed protein ligation", Chemical Communications, issue 7: 822-823) disclose a protein-nucleic acid conjugate where a recombinant protein is designed with an intein sequence which uses DNA directed immobilization. An intein is an approximately 150 amino acid polypeptide sequence which can excise itself "from a primary translation product with concomitant ligation of the flanking polypeptides (exteins)" (Cook et al., 1995, "Photochemically Initiated protein splicing", Angewandte Chemie International Edition in English, vol. 34(15):1629-1630) In this paper Lovrinovic used an expressed protein containing a recombinant protein with a covalently bound intein sequence followed by a chitin binding domain. This multifunctional protein hybrid molecule was first purified using the chitin binding domain on a chitin column. Additional molecules containing chemically synthesized cysteine peptides covalently bound to synthetic oligonucleotide sequence are added to the reaction after purification and are bound to the carboxy terminus of the recombinant protein after the excision of the intein region by transesterification followed by ligation of the chemically ligated cysteine-synthetic oligonucleotide hybrid. This now generates a molecule with recombinant protein covalently bound to the cysteine-synthetic oligonucleotide hybrid with no intein sequence. This new molecule can then be used to bind antigen (the recombinant protein) to a complementary synthetic oligonucleotide bound to a solid support, much like DDI technology where the antibody is replaced in this application with an antigen or recombinant protein molecule.

Fan et al., 2008 ("Integrated Barcode chips for rapid, multiplexed analysis of protein in microliter quantities of blood", Nature Biotechnology, Advance Online Publication) describe yet another variation of this DDI technology.

Heyduk et al., (2008, "Molecular Pincers: Antibody-Based Homogeneous Protein Sensors", Analytical Chemistry, vol. 80:5152-5159) describes a Fluorescence Resonance Energy Transfer (FRET) based antibody detection technology wherein one antibody molecule with associated first synthetic oligonucleotide which possesses a donor chromophore, and a second antibody molecule which binds to the same antigen at another site on the antigen and which possesses an associated second synthetic oligonucleotide which is complementary to the first synthetic oligonucleotide sequence which possess an acceptor chromophore. The close proximity of the two antibodies on the antigen permit the synthetic oligonucleotide sequences to hybridize and in turn bring the donor and acceptor chromophores in close proximity to each other which reduces the resulting fluorescence. This is a homogeneous antigen detection approach and does not employ a capture antibody.

Niemeyer et al., (2002, "DNA-directed Assembly of Bienzymic complexes from In Vivo Biotinylated NAD(P)H:FMN Oxidoreductase and Luciferase", (ChemBio Chem, No 02-03: 242-245) describe spatially ordered multienzyme complexes (MECs) using DNA-directed organization, but is silent on the development of ELISA and more sensitive immunoassay tests.

Seeman, (1999, "DNA engineering and its application to nanotechnology", TIBTECH, vol 17:437-443) describes the application of DNA scaffolding wherein complementary synthetic oligonucleotide sequences can be designed to generate unique structures, but is silent on ELISA assays.

Niemeyer, (2000, "Self-assembled nanostructures based on DNA: towards the development of nanobiotechnology", Current Opinion in Chemical Biology, vol 4: 609-618) describes the application of DNA to generate scaffolding backbones for ordered structures, but is silent on ELISA and other more sensitive immunoassays.

Storhoff & Mirkin, (1999, "Programmed materials synthesis with DNA", (Chemical Review, vol. 99: 1849-1862) describes the use of DNA as a scaffolding material but is silent on its use for ELISA assays.

Niemeyer et al., (1998, "Covalent DNA-Streptavidin Conjugates as Building Blocks for novel Biometallic Nanostructures", Angew. Chem. Int. Ed., vol. 37(16): 2265-2268) describes the use of DNA scaffolds to generate structured molecules with multi-streptavidin molecule aggregates using a biotin streptavidin immunoglobulin attached to this aggregate of biometallic aggregates.

Tomkins et al., (2001, "Preparation of Symmetrical and Unsymmetrical DNA-Protein Conjugates with DNA as a molecular Scaffold", ChemBio Chem, Issue 5: 375-378), describe generating Streptavidin-DNA conjugates which were imaged by atomic force microscopy for streptavidin-DNA dumb-bells. This reference is silent on ELISA and other sensitive immunoassays.

Takeda et al., (2008, "Covalent split protein fragment-DNA hybrids generated through N-terminus specific modification of proteins by oligonucleotides", Organic and Biomolecular Chemistry, vol. 6:2187-2194) describe the use of DNA hybrids attached to split proteins to form active enzyme molecules, but do not anticipate ELISA or other sensitive immunoassays.

Niemeyer et al., (1994, "Oligonucleotide-directed self-assembly of proteins: semi-synthetic DNA-streptavidin hybrid molecules as connectors for the generation of macroscopic arrays and the construction of supramolecular bioconjugates", Nucleic Acids Research, vol. 22(25): 5530-5539) describe a hybrid between an antibody and ALP enzyme using a biotinylated antibody and a biotinylated alkaline phosphatase and streptavidin attached to two DNA sequences wherein the two proteins are bound to each other through biotin-streptavidin binding. This invention describes two molecules scaffolded together directly through DNA hybridization using terminal streptavidin molecules binding to biotinylated antibody and alkaline phosphatase molecules. As the terminal binding moiety is streptavidin, it does not afford the level of controlled synthesis as would be found for covalently bound synthetic oligonucleotide sequences, as for example, the multivalent streptavidin molecule could bind either an antibody or alkaline phosphatase molecule which is biotinylated.

Duckworth et al., (2007, "A Universal Method for the preparation of Covalent Protein-DNA Conjugates for use in Creating Protein Nanostructures", Angew. Chem. Int. Ed. Vol. 46: 8819-8822) describe the use of DNA-protein structures as scaffolding structures to precisely attach green fluorescent protein, but are silent on ELISA and other immunoassay technology.

Niemeyer, (2000, "Self-assembled nanostructures based on DNA: towards the development of nanobiotechnology", Current Opinion in Chemical Biology, vol. 4:609-618) describes the use of protein assembled structures using Covalently attached DNA, but is silent on ELISA and other immunoassay technology.

Kawabata et al., (2005, "Liquid-Phase Binding Assay of alpha-Fetoprotein Using DNA-Coupled Antibody and Capillary Chip Electrophoresis", Analytical Chemistry, vol. 77: 5579-5582) developed a chromatography based immunoassay wherein they added a DNA conjugated antibody molecule with antigen and determined the presence of antigen binding by the increased molecular weight after chromatography, and in this particular assay they used capillary electrophoresis. This method does not use a capture antibody, nor an enzyme-linked conjugate as used in an ELISA assay and therefore differs from the present invention.

Zhang & Guo, (2007, "Multiple labeling of Antibodies with Dye/DNA Conjugate for Sensitivity Improvement in Fluorescence Immunoassay", Bioconjugate Chemistry, vol. 18(5): 1668-1672) describe a method of immuno-detection that first requires fixing the antigen to a solid support, followed by the addition of a biotinylated antibody, which then uses a biotin-streptavidin-biotin moiety attached to a synthetic oligonucleotide which is fluorescently labeled. This concept differs from the present invention.

Zhu et al. (2008, "Part-per-trillion level detection of estradiol by competitive fluorescence immunoassay using DNA/dye conjugate as antibody multiple labels", Analytica Chimica Acta, vol. 624:141-146) used fluorescently tagged DNA to increase signal. The synthetic oligonucleotide contains multiple fluorescent tags and biotin bound to streptavidin, which in turn is bound to biotinylated antibodies. The purpose of this construct was to increase the number of fluorescent tags associated with the antibody and in turn increase the signal level. This differs from the present invention for at least the reason that the synthetic oligonucleotides are covalently attached to the antibody.

Niemeyer et al., (2001, "Nanostructured DNA-Protein Aggregates Consisting of Covalent Oligonucleotide-Streptavidin Conjugates", Bioconjugate Chemistry, vol. 12(3): 364-371) have generated nanostructures of multimers of streptavidin-biotin-DNA-biotin-streptavidin-biotin-DNA-biotin-streptavidin which binds to biotinylated antibodies to generated structures for use in immuno-PCR reactions. This differs from the present invention.

Kujipers et al., (1993, "Specific Recognition of Antibody-Oligonucleotide Conjugates by Radiolabeled Antisense Nucleotides: A Novel Approach for Two-Step Radioimmunotherapy of Cancer", Bioconjugate Chemistry, vol. 4: 94-102) generated DNA antibody conjugates which were used for "pre-targeted" radio immunotherapy of cancer patients. This allowed the addition of non-radioactive DNA antibody conjugates to targeted sites, followed by radiolabelled complementary DNA, allowing very specific radiation therapy. The present invention does not deal with radio immunotherapy.

BRIEF SUMMARY OF THE INVENTION

In a first aspect, the invention is directed to a single-use cartridge for performing an immunoassay comprising a sample entry port for receiving a biological sample suspected of containing a target analyte, e.g., antigen, a conduit containing an electrode, a region containing a wash fluid, and a waste chamber. A sandwich assay is formed on the electrode. The sandwich assay comprises an immobilized first antibody bound to the target analyte, e.g., antigen, a second antibody to the target analyte, e.g., antigen, wherein the second antibody is attached to a first single stranded nucleotide; and one or more signal elements (e.g., signal enzymes or fluorescent dyes) each attached to a second single stranded nucleotide having complimentary base pairs to the first single stranded nucleotide. The wash fluid is capable of washing the biological sample from the electrode in the conduit into the waste chamber. In embodiments where the signal element is a signal enzyme, the cartridge further comprises a region containing an enzyme substrate capable of reacting with the signal enzyme to generate a signal at the electrode proportionate to the amount of the target antigen in the biological sample.

In a second aspect of the present invention, there is provided a composition of matter for use in an immunoassay comprising: a FAB fragment covalently linked to a first nucleotide; and one or more signal elements (e.g., signal enzymes or fluorescent dyes) each covalently linked to a second nucleotide, wherein said first nucleotide has one or more repeated sequences, and wherein the second nucleotide is bound to one of the one or more repeated sequences on said first nucleotide, and wherein the ratio of the FAB fragment to the signal element is controlled by the number of repeated sequences.

In a third aspect of the present invention, there is provided a method of determining the presence of analyte in a biological sample comprising: contacting the biological sample so that the analyte binds to an immobilized first antibody and a second antibody to form an immunoassay, wherein the second antibody is bound to at least one signal enzyme via a synthetic nucleotide bridge; washing said biological sample from said conjugate; and determining the presence of the analyte based on the signal generated by a reacting with the signal enzyme.

In a fourth aspect of the present invention, there is provided a method of determining whether a patient may suffer a myocardial infarction comprising: (a) applying a sample from a patient to a surface to which is bound a first antibody which is capable of binding to a first epitope on cTnI; (b) adding a second antibody that is capable of binding to a second epitopes on cTnI, wherein the second antibody further comprises a first stranded polynucleotide sequence that binds to one or more second stranded polynucleotides bound to a signal element (e.g., signal enzyme or dye); and (c) determining the extent of binding of the at least second antibodies

BRIEF DESCRIPTION OF THE DRAWINGS

The foregoing and other objects and advantages of our invention will appear more fully from the following description, made in connection with the accompanying drawings of non-limiting preferred embodiments of the inventions, wherein like characters refer to the same or similar parts throughout the views, and in which:

FIG. 16A-16C represent of antigen analytical detection based on signal amplification from a nucleic acid strand displacement step;

FIG. 28: S300 Columns fractions from PEP-3 F(ab')2 LC-SPDP reacted with DTT treated A synthetic oligonucleotide;

FIG. 29: Chronoamperometric plot of production version of cTnI cartridge using analyte competition from addition of free antibody or conjugate to the sample used. [1] MWC 92353 diluted to 2.59 ng/ml and used 2 μL [5.2 pg]. [2] Analyte with addition of 49.2 ng PEP-3 F(ab), [3] Analyte with addition of 61.8 ng PEP-4 F(ab), [4] Analyte with addition of 109 ng E0031 conjugate;

DETAILED DESCRIPTION OF THE PREFERRED EMBODIMENTS

Figure 1:
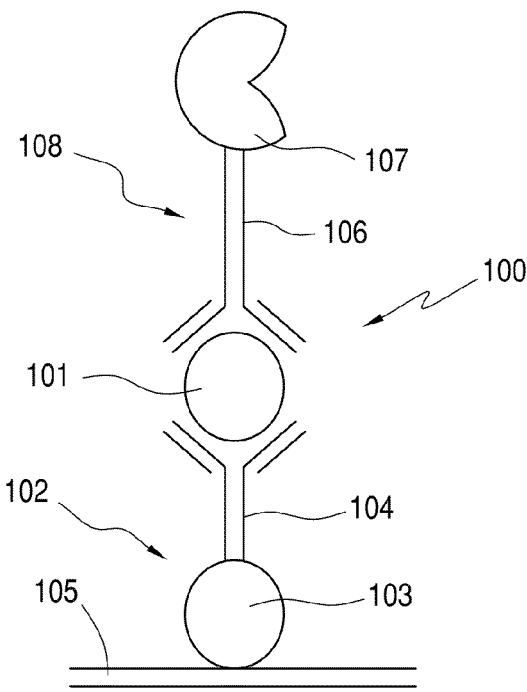
FIG. 1 is a representation of a standard sandwich assay for detecting an analyte of interest.

In various embodiments, the present invention is directed to devices and methods for making and using signal conjugates having a substantially narrow and/or controllable ratio or stoichiometry, by using decorated strands of complimentary nucleotide sequences. The signal antibodies preferably are bound to the signal elements with complementary strands of DNA. As used herein, the term "signal conjugate" refers to one or more signal antibodies bound to one or more signal elements. By "signal element" it is meant an element capable of indicating the presence of an analyte, e.g., antigen, when bound thereto via a signal antibody. Examples of signal elements include, for example, signal enzymes, such as alkaline phosphatase (ALP), and fluorescent dyes. In preferred embodiments, the signal conjugate comprises one or more (preferably a pair of) Fragment Antigen Binding (FAB) antibody fragments bound to one or more ALP molecules. The present labeling method leads to a high degree of control over the ratio of signal antibodies, e.g., FAB fragments, to signal elements, e.g., signal enzymes such as ALP or fluorescent dyes, to the number of signal antibodies per signal conjugate and to the number of signal elements per signal conjugate.

Traditional sandwich assays usually form a variable ratio of signal antibodies to signal element (e.g., FAB to ALP) of from 0-15 ALP for each FAB, as well as the number of signal antibodies and signal elements, respectively, per signal conjugate. Due to these variable ratios, it is difficult to obtain a predictable signal which may be more sensitive to low levels of analyte in the biological sample.

In one embodiment, the average number of signal elements, e.g., signal enzyme such as ALP or fluorescent dye, per signal conjugate ranges from about 1 to about 100, e.g., from 1 to about 5, e.g., from about 5 to about 10, or from about 10 to about 100, while retaining a high diffusion coefficient compared to large agglomerates. Preferably these ranges are achievable without a step of separating signal conjugates, e.g., through size exclusion chromatography, to arrive at signal conjugates having the desired number of signal elements per signal conjugate. In addition, such signal conjugates, e.g., FAB-ALP conjugates, may be useful in immunoassays where having a controllable ratio of ALP to FAB allows an operator to obtain highly predictable results. Predictable results may lead to improvements in the sensitivity of the immunoassay and hence reliable detection of lower levels of a target analyte such as cTnI.

The signal conjugates also preferably have a narrow distribution of ratios of signal elements to signal conjugates, which provides for improved accuracy of the detection devices and methods. For example, in various embodiments, at least 50 wt. %, e.g., at least 70 wt. %, at least 90 wt. % or at least 95 wt. % of the signal conjugates formed or used in the detection device or method have from 5 to 10 signal elements per signal conjugate. In another embodiment, at least 50 wt. %, e.g., at least 70 wt. %, at least 90 wt. % or at least 95 wt. % of the signal conjugates formed or used in the detection device or method have from 1 to 5 signal elements per signal conjugate. In still another embodiment, at least 50 wt. %, e.g., at least 70 wt. %, at least 90 wt. % or at least 95 wt. % of the signal conjugates formed or used in the detection device or method have from 10 to 100 signal elements per signal conjugate.

Figure 5:
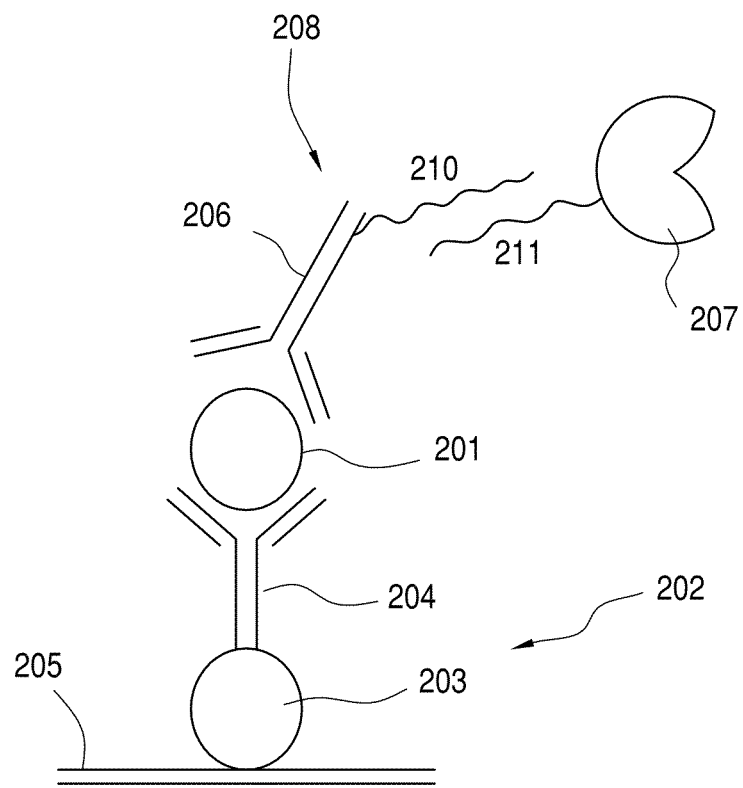
FIG. 5 is a representation of electrochemical detection of analyte using a DNA conjugate based according to an embodiment of the present invention.

In addition, reduced F(ab)'2 signal conjugates preferably contain a single signal antibody per signal conjugate. Conventional techniques for forming signal conjugates, however, may lead to the formation of signal conjugates having a wide distribution in the number of signal antibodies (e.g., 0-4 or more) per signal conjugate. The average number of signal antibodies, e.g., reduced F(ab)'2 fragments, per signal conjugate according to the processes and devices of the invention preferably ranges from 1 to 4, and preferably is 2, as illustrated in FIG. 5. Preferably these ranges are achievable without a step of separating signal conjugates, e.g., through size exclusion chromatography, to arrive at signal conjugates having the desired number of signal antibodies per signal conjugate.

The signal conjugates also preferably have a narrow distribution of ratios of signal antibodies to signal conjugates, which provides for improved accuracy of the detection devices and methods. For example, in various embodiments, at least 50 wt. %, e.g., at least 70 wt. %, at least 90 wt. % or at least 95 wt. % of the signal conjugates formed or used in the detection device or method have from 1 to 4 signal antibodies per signal conjugate. In a preferred embodiment, at least 50 wt. %, e.g., at least 70 wt. %, at least 90 wt. % or at least 95 wt. % of the signal conjugates formed or used in the detection device or method have 2 signal antibodies per signal conjugate.

According to various embodiments of the present invention, the signal conjugates also preferably have a high degree of controllability in the overall ratio of signal elements to signal antibodies in the population of signal conjugates. In some exemplary embodiments, the average number ratio of signal elements, e.g., signal enzymes such as ALP or fluorescent dye, to signal antibodies, e.g., FAB fragments individually and in the overall population of signal conjugates ranges from 0.5 to 100, e.g., from 0.5 to 5, e.g., from 5 to 10 or from 10 to 100. Again, these ranges preferably are achievable without a step of separating signal conjugates, e.g., through size exclusion chromatography, to arrive at signal conjugates having the desired ratio of signal elements to signal antibodies.

The signal conjugates also preferably have a narrow distribution of number ratios of signal elements to signal antibodies per signal conjugate, which provides for improved accuracy of the detection devices and methods. For example, in various embodiments, at least 50 wt. %, e.g., at least 70 wt. %, at least 90 wt. % or at least 95 wt. % of the signal conjugates formed or used in the detection device or method have a number ratio of signal elements to signal antibodies ranging from 1 to 5. In a preferred embodiment, at least 50 wt. %, e.g., at least 70 wt. %, at least 90 wt. % or at least 95 wt. % of the signal conjugates formed or used in the detection device or method have a number ratio of signal elements to signal antibodies ranging from 5 to 10. In another preferred embodiment, at least 50 wt. %, e.g., at least 70 wt. %, at least 90 wt. % or at least 95 wt. % of the signal conjugates formed or used in the detection device or method have a number ratio of signal elements to signal antibodies ranging from 10 to 100.

The diffusion coefficient of the signal conjugates preferably is low enough in order to provide efficient transport of the signal conjugates in the detection device. Lower diffusion coefficients reduce the time required for sandwich immunoassay formation. Reducing the time for formation the immunoassay improves the efficiency of the test in real time while also increasing sensitivity. In some exemplary embodiments, the diffusion coefficient of the signal conjugates ranges from about $1 \times 10^{-8}$ to about $1 \times 10^{-6}$ cm$^2$/s (Brune & Kim, 1993, Proceedings of the National Academy of Sciences, vol. 90: 3835-3839).

The target analyte to be detected may vary widely. In some exemplary embodiments, the analyte, is selected from TnI, TnT, TnC, CK-M, CK-B, CK-MB, myoglobin, TSH, FSH, CRP, BNP, pro-BNP, PSA, PCA, apolipoprotein, and combinations thereof. The target analyte may be an antigen. Although the present invention will be described in terms of cTnI as the target analyte, the embodiments of the present invention are not limited to detecting cTnI and, as will be appreciated by those skilled in the art, the invention may be employed to detect other analytes as well. Embodiments of the present invention generally relate to improved sensor devices and methods that have an increased sensitivity to measuring cardiac Troponin I (cTnI) in biological samples, including blood samples.

cTnI is now used as an accurate cardiac-specific biological parameter detectable in serum very soon after active myocardial infarction (MI) and remaining present for more than 2-3 days after the onset of MI. Troponin is present in cardiac tissue as a complex of three subunits: Troponin T ("TnT"), the tropomyosin binding subunit, Troponin C ("TnC"), the $Ca^{2+}$ binding subunit; and Troponin I ("TnI"), the sub-unit which inhibits the actomyosin $Mg^{2+}$ ATPase. TnI is a thin filament regulatory protein complex, which confers calcium sensitivity to the cardiac and striated muscle. Cardiac TnI is uniquely located in the myocardium where it is the only isoform present. Cardiac TnI rapidly appears in human serum (within approximately 4 to 6 hours) following a MI. It reaches a peak level after 18-24 hours and remains at elevated levels in the blood stream for up to 6-10 days. As a result, cTnI released into the circulation from the myocardium is very specific for myocardial injury. In one embodiment, the sensors and devices of the invention are useful in detecting very low levels of cTnI, which require greater sensitivity. As discussed above, even very low levels of cTnI, i.e., below those considered indicative of acute myocardial infarction, may be indicative of future adverse cardiovascular status. In some exemplary embodiments, the present invention provides devices and methods capable of detecting cTnI in amounts less than 10 pg/mL, e.g., less than 1 pg/mL or less than 0.1 pg/mL, thereby providing the ability to predict myocardial infarction.

Antigen and/or analytes (An) 101 have traditionally been detected using systems and processes based on sandwich assays 100 as depicted in FIG. 1, as described in US Pub. No. 2004/0018577, the entirety of which is incorporated herein by reference. For purpose of the present application antigen and/or analytes 101 will generally refer to troponin cTnI, but other types of antigens and/or analytes may be detected by assays. A capture bead 102 comprising a carboxyl derivatized polystyrene bead 103 with a covalently attached capture antibody (Ab1) 104, or antibodies or binding fragment thereof, is situated over a metal electrode 105 typically made of gold or platinum. During an analytical assay, an antigen 101 found in a test sample such as blood is bound by the capture antibody 104. A detection antibody (Ab2) 106, antibodies or binding fragment thereof; is conjugated to a signal generating enzyme (ENZ) 107, such as alkaline phosphatase (ALP). For conventional signal elements, a crosslinking agent, such as a succinimidyl-4-[N-maleimidomethyl]-cyclohexane-1-carboxy[6-amid-ocaproate], glutaraldehyde, adipic acid dihydrazide, bis-diazotized benzidine, 1,4-butane diglycidyl ether, bis-maleimido hexane, sulfosuccinimidyl 4-(N-maleimidomethylcyclohexane-1-carboxylate, or N-hydroxysuccinimidyl 4-azidosalicylic acid, may be used to label the Ab2 with ENZ. For more information on commercial immunoassay products and the technology on which they are based, see Wild, (Ed), The Immunoassay Handbook, Stockton Press N.Y., 1994, which is incorporated herein by reference. Detection antibody 106 and enzyme 107 are covalently linked and form a detection antibody conjugate 108. The assembly of conjugate 108 enables the electrogenic species generated by the enzyme 107 described in the above referenced U.S. Pat. No. 7,419,821, to be in close proximity to the metal electrode 105, in turn generating an electrochemical signal to be generated. The An is attached to the respective Ab1 and Ab2 through epitopes (e1 and e2).

Figure 2:
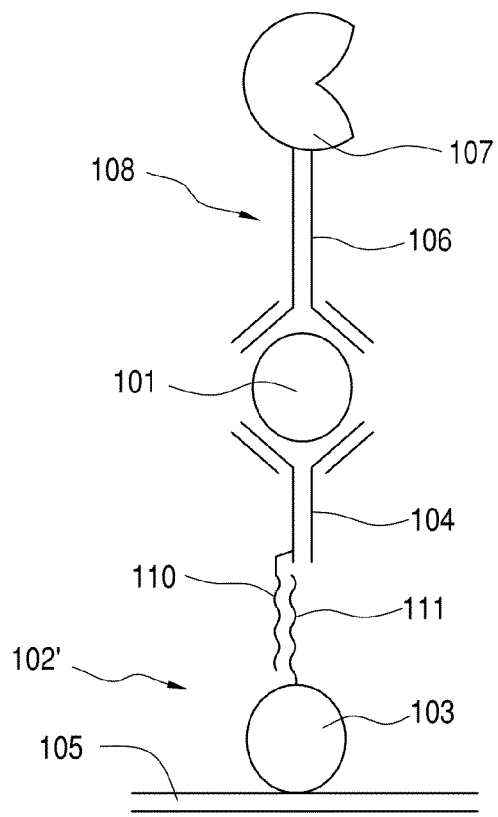
FIG. 2 is a representation of a standard DNA-directed immobilization for detecting an analyte of interest.

DNA-directed immobilization (DDI) is another conventional detecting system of antigens 101 is depicted in FIG. 2. A capture bead 102' comprising a carboxyl derivatized polystyrene bead 103 with a covalently attached nucleic acid 111 situated over a metal electrode 105 typically made of gold or platinum. A capture antibody 104, antibodies or binding fragment thereof, is covalently bound to a nucleic acid 110. The nucleic acids depicted as 110 and 111 have regions of complementarily which creates a stable region of hybridized double stranded DNA. It will be understood by those skilled in the art that covalent attachment of protein and nucleic acids can occur at the 5' or 3' termini or through a modification of one or more bases. During an analytical assay using DDI, the detection is similar to the process described for FIG. 1. The detection antibody 106 of the detection conjugate 108 binds to the antigen 101 and the enzyme 107 generates a signal that is detected by electrode 105.

Figure 3:
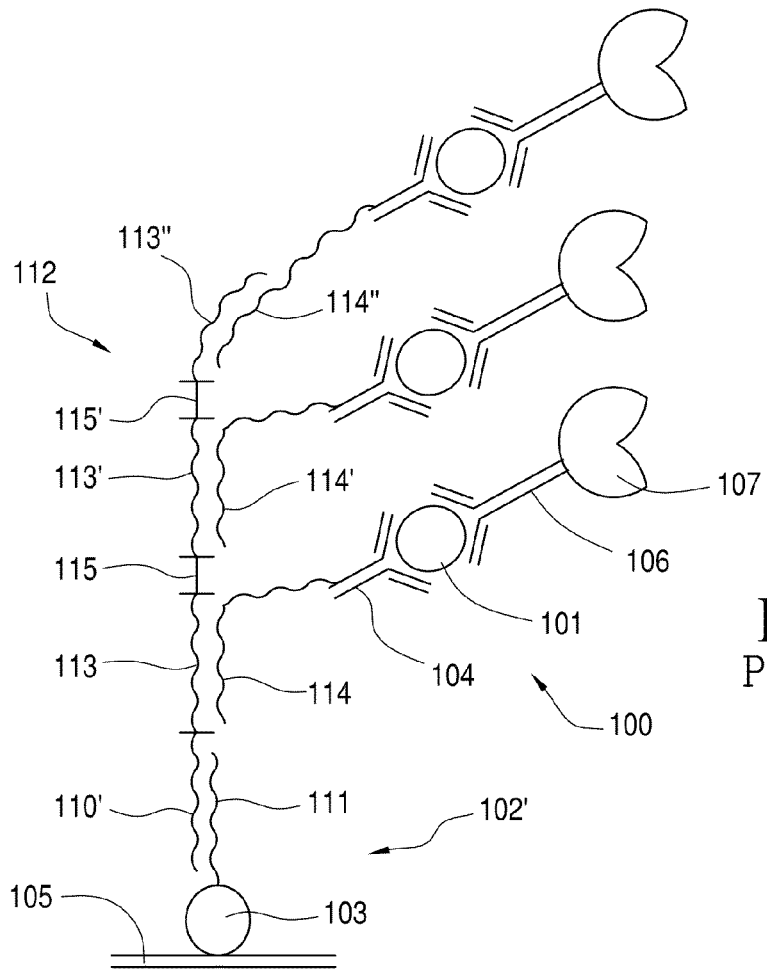
FIG. 3 is a representation of a standard DNA-directed immobilization for detecting an analyte of interest.

Another conventional detection system is shown by the DNA-directed immobilization represented in FIG. 3. A capture bead 102' comprising a carboxyl derivatized polystyrene bead 103 with a covalently attached nucleic acid 111 situated over a metal electrode 105 typically made of gold or platinum. A nucleic acid sequence 112 having the characteristics of a region 110' permitting hybridization to the nucleic acid 111 bound to the capture bead 103, a sequence 113 for hybridization to the complementary nucleic acid sequence 114 associated with the antibody sandwich structure 100, described above in reference to FIG. 1, and an optional spacer sequence 115. As shown in FIG. 3, there may be multiple sequences 113', 113" that hybridizes to complementary nucleic acid sequence 114', 114" to attach multiple sandwich structures. Further spacer sequences 115' may separate each sequence 113 on nucleic acid 112. Although three sandwich structures 100 are shown in FIG. 3, in other DNA-directed immobilization there may be more sandwich structures 100 bound through nucleic acid sequence 112. Capture antibody 104 is covalently attached to nucleic acid sequence 114. Antigen 101 is captured by capture antibody 104 and a detection antibody 106, having an enzyme 107, binds to the captured antigen 101, as described above.

Figure 4:
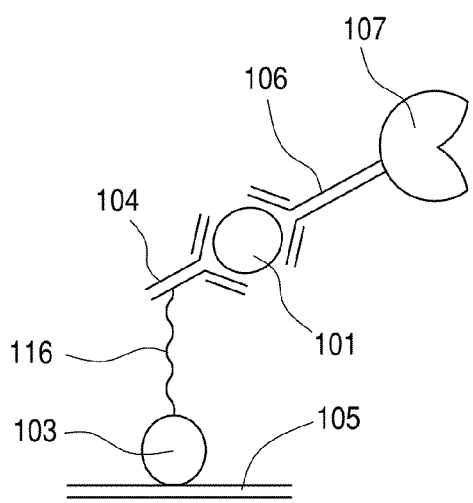
FIG. 4 is a representation of a standard detecting assay having nucleic acid bound to the bead.

One derivative of the conventional detecting assays is shown in FIG. 4. Nucleic acid 116 is covalently attached to bead 103 over electrode 105. Capture antibody 104 is covalently bound to the nucleic acid 116, effecting additional flexibility of this capture species. Antigen 101 is detected by detection antibody 106 and enzyme 107 as described above.

In one embodiment of the present, an analysis scheme is provided for the detection of low concentrations of immunoactive analytes, such as cTnI. The analysis scheme relies on the formation of a signal conjugate in which one or more signal antibodies (preferably a pair of signal antibodies) are bound via a DNA linkage to one or more signal elements. A signal antibody in the signal conjugate binds with an analyte, which binds in turn with a capture antibody to form a "sandwich" complex. Depending on the signal element employed, the concentration of analyte in a sample may be converted into a proportional signal. For example, if the signal element comprises a signal enzyme such as ALP, then the concentration of analyte in the sample may be converted into a proportional surface concentration of the signal enzyme. The enzyme is capable of amplifying the analyte's chemical signal by converting a substrate to a detectable product. For example, where ALP is the enzyme, a single enzyme molecule can produce about nine thousand detectable molecules per minute, providing several orders of magnitude improvement in the detectability of the analyte compared to schemes in which an electroactive species is attached to the antibody in place of alkaline phosphatase.

Figure 6:
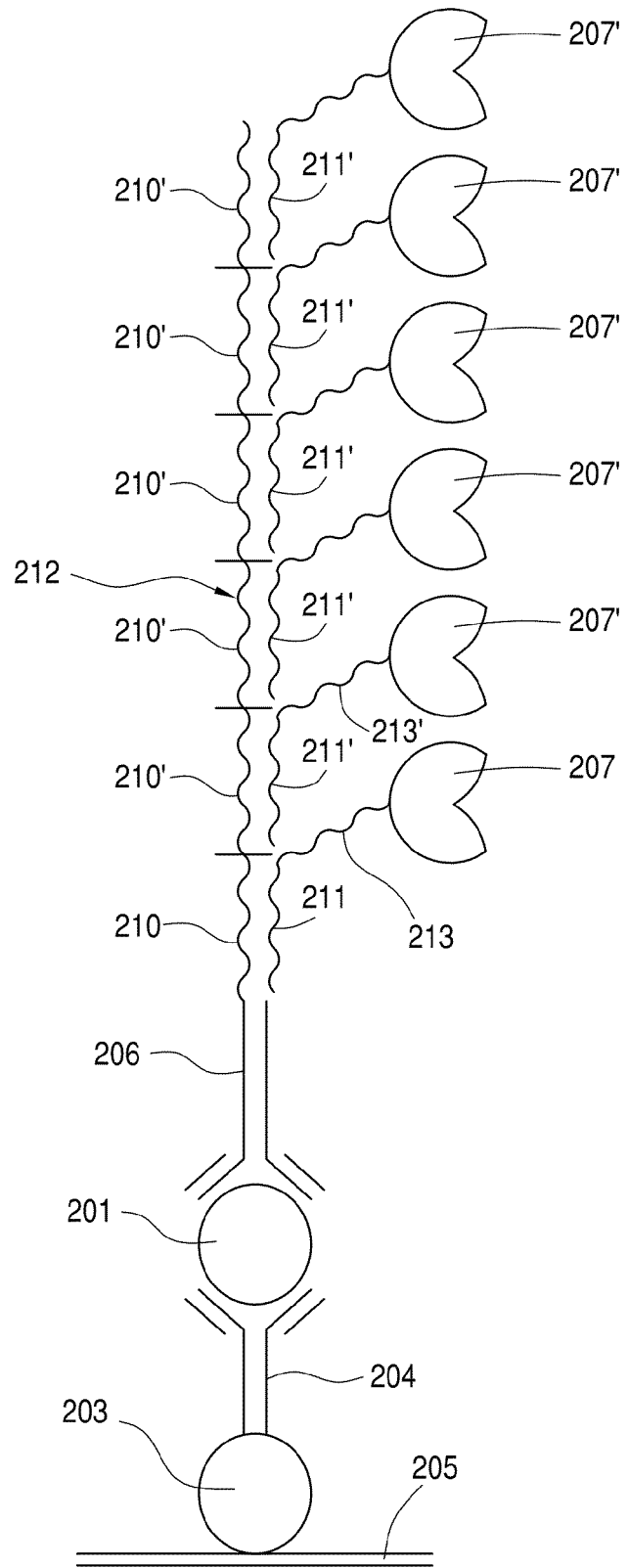
FIG. 6 is a representation of electrochemical detection of analyte using a polymer DNA scaffold to combine multiple enzyme species as a conjugate according to an embodiment of the present invention.

To detect low levels of target analyte 201, such as cTnI, a novel capture antibody process may be employed such as those shown in FIGS. 5 and 6. As shown, a capture bead 202 comprising a carboxyl derivatized polystyrene bead 203 with a covalently attached antibody 204 is situated over a metal electrode 205. The "capture antibody" 202 or "capture reagent" means an antibody that specifically binds to an epitope of an analyte of interest 201, wherein the capture antibody 204 is immobilized on a bead 203 either (i) before, (ii) after or (iii) during binding to the analyte of interest 201. A detection or signal antibody 206, which is not immobilized on the bead 203, binds to an additional epitope of the analyte 201 of interest, if present in the biological sample. Initially, the signal antibodies 206 may be disposed in a solubilizing agent, e.g., sugar matrix, within a conduit in the device (e.g., downstream of where the sample is introduced in the device, but upstream of the immobilized capture antibodies) such that when the sample contacts the solubilizing agent, the signal antibodies 206 are solubilized into the sample. Antibodies 204, 206 used with the present invention may comprise a full length antibody, a single-chain antibody, or an antibody fragment, such as a FAB fragment. One of skill in the art will recognize that the invention described herein may detect an analyte of interest 201 by using any binding member that is capable of specifically binding to an epitope on the analyte of interest 201. Binding members include, but are not limited to, extracellular or intracellular receptors, polynucleotides, peptide nucleic acids, and derivatives thereof.

Covalently attached to the signal antibody 206 is a first single stranded nucleotide 210. A signal element 207, e.g., signal enzyme of fluorescent dye, is covalently attached to a second single stranded nucleotide 211, which is complementary to the first single stranded nucleotide 210. The first 210 and second 211 single stranded nucleotides are synthetic nucleotides and may contain a coupling moiety at the 5' end, 3' end or internal to the nucleotide sequence. The coupling moiety may be generated from a modified phosphoramidite selected from the group consisting of an amino modifier, thiol modifier, and dithiol. The 3'-end or 5'-end of the synthetic oligonucleotides is protected from endogenous exonuclease activity in the sample by incorporating a protective chemical group, such as a phosphorothioate (or S-oligos). Antibody 206, enzyme 207, first 210 and second 211 single stranded nucleotides comprise a detection antibody conjugate 208.

In embodiments where the signal element is a signal enzyme, the signal enzyme preferably is selected from the group consisting of alkaline phosphatase (ALP), glucose oxidase, lactate oxidase, urease, horseradish peroxidase, galactose oxidase, and beta-galactosidase. In a preferred embodiment, ALP is the signal enzyme.

In various alternative embodiments, the one or more signal elements comprise one or more non-enzymatic detection moieties. Examples of non-enzymatic detection moieties include fluorescent, colorimetric, and radioactive elements, species or dyes, specific examples of which include 6-FAM (6-carboxyfluorescein), radioactivity, or quantum dots.

In one embodiment, the first and second stranded nucleotide are synthetic oligonucleotides having from 18-10,000 base residues. In one preferred embodiment each sequence has a spacer, such as repeating base residues, to allow the signal conjugate, e.g., FAB-ALP conjugate, to form. The first and second stranded nucleotides hybridize to form a bridge between the signal antibody and the signal element, e.g., ALP, as shown in FIG. 5.

In one embodiment, a portion of a repeating first stranded nucleotide 210, 210' binds to a plurality of second stranded nucleotides 211, 211' to form the DNA scaffolding or multimer structure 212 as shown in FIG. 6. Each portion of the first stranded nucleotides 210, 210' may be a repeated sequence. The second stranded nucleotides 211, 211' bind to available portions of the first stranded nucleotides 210, 210'. For example, with FAB:ALP conjugates, a ratio of 1:5 (FAB: ALP) may be achieved by a first stranded nucleotide 210, 210' having five repeating sequences which bind with five second sequences 211, 211' each attached to ALP 207, 207'. In one embodiment, the first nucleotide 210 has at least three repeated sequences which bind to at least three of the second sequences 211 of at least three of the one or more signal enzymes 207. In one embodiment, the first nucleotide 210 has at least five repeated sequences which bind to at least five of the second sequences 211 of at least three of the one or more signal enzymes 207. In one embodiment, there are at least two different portions of the first stranded nucleotide 210 for binding with different signal elements 207, e.g., signal enzymes or fluorescent dyes.

Optionally, one or more spacing sequences (not shown) may separate first stranded nucleotides 210, 210' and/or second stranded nucleotides 211, 211'. Second stranded nucleotides 211, 211' may also have a spacing sequence 213, 213' that binds to enzyme 207.

In one embodiment, DNA scaffolding 212 of FIG. 6 may amplify the signal generated by enzymes 207, 207' when a detecting antibody 206 binds to antigen 201.

Figure 7:
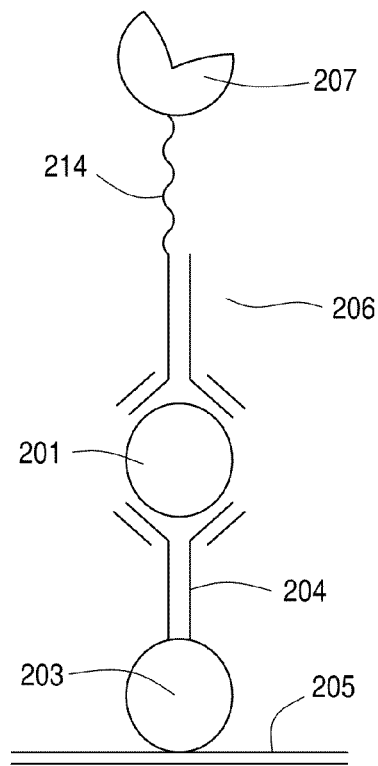
FIG. 7 is a representation of electrochemical detection of analyte using a DNA bound to the detecting antibody and signal enzyme based according to an embodiment of the present invention.

FIG. 7 represents an embodiment of the present invention in which detection antibody 206 is covalently bound to a nucleic acid sequence 214 which is additionally covalently bound at its other terminus of its sequence to the enzyme 207. This increases the flexibility of this structure.

Figure 8:
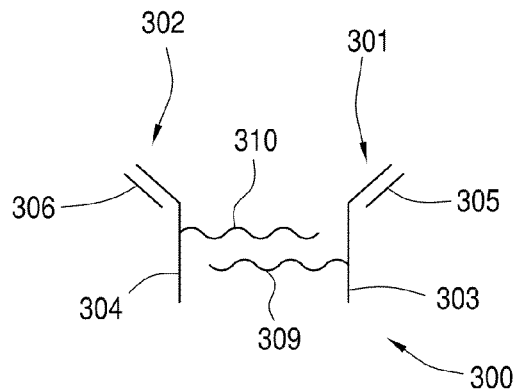
FIG. 8 is a representation of antibodies species covalently linked using DNA according to an embodiment of the present invention.

FIG. 8 is a detailed representation of antibody 300. Antibody 300 may be a detection or capture antibody as described throughout the present application. Antibody 300 comprises two antibody species 301 and 302. Each two antibody species 301, 302 comprises a long chain or fragment 303, 304 and a light chain 305, 306. Antibody species 301 is covalently bound to nucleic acid sequence 309. Antibody species 302 is covalently bound to nucleic acid sequence 310. Nucleic acid sequences 309 and 310 have a binding region which are hybridizable. In one embodiment, antibody species are different and are joined together through the hybridization event. Antibody species 301 and 302 can recognize the same epitope, different epitopes on the same antigen, or different antigens.

Figure 9:
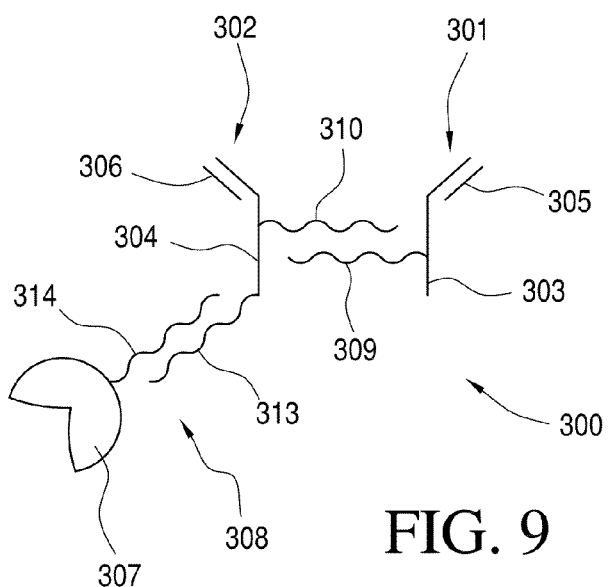
FIG. 9 is a representation of antibodies species covalently linked using DNA and attached to an enzyme according to an embodiment of the present invention.

FIG. 9 is another detailed representation of antibody 300 that comprises a conjugate 308 having an enzyme 307. The long chain 304 of species 302 is covalently bound to nucleic acid sequence 313. Enzyme 307 is covalently bound to nucleic acid sequence 314. Nucleic acid sequences 313 and nucleic sequence 314 have a binding region which are hybridizable. It would be appreciated by those skilled in the art that the nucleic acid sequence covalently may be bound to the long chain of either species. Additionally, both antibody species shown in FIG. 9 could have different or same sequences covalently bound to them. Where the sequences are different, a different complementary sequence with associated functionality, such as a different enzyme conjugate, could be used.

Figure 10:
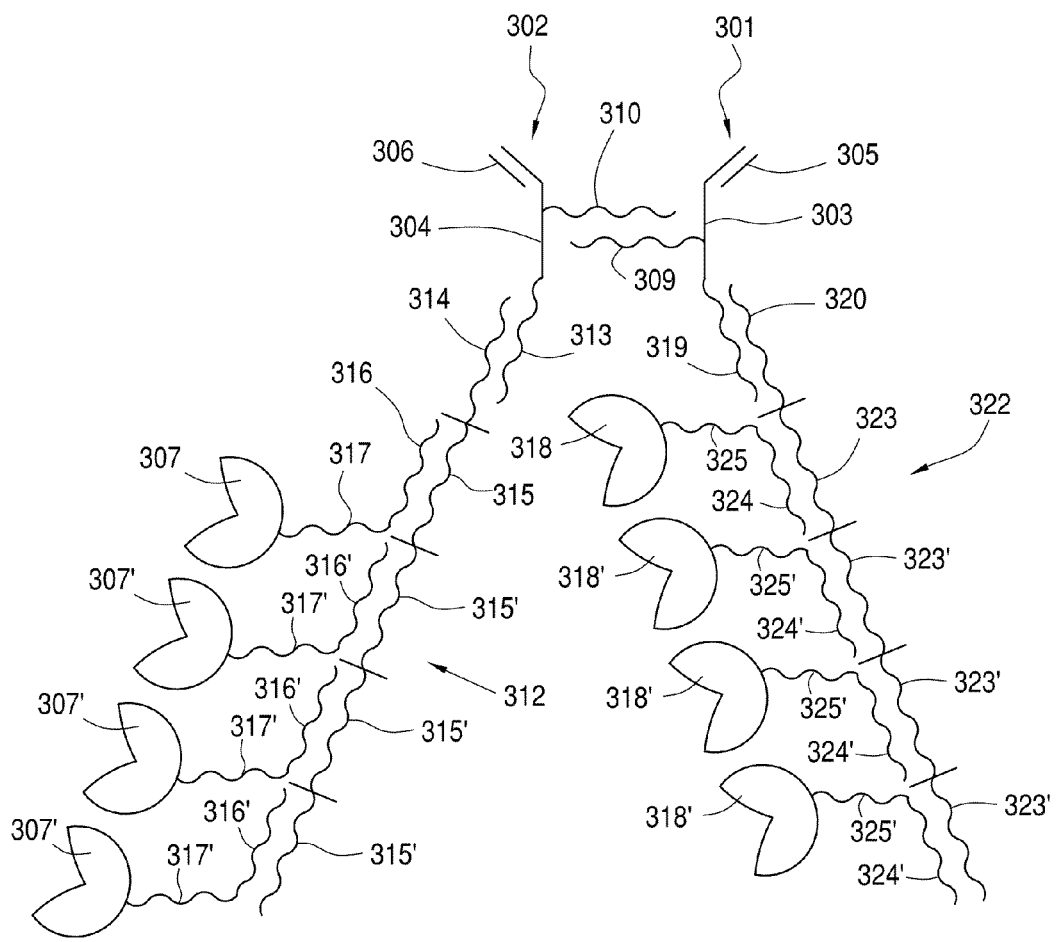
FIG. 10 is a representation of antibodies species covalently linked using DNA and having DNA scaffolding attached to each species according to an embodiment of the present invention.

In one embodiment, a portion of a first stranded nucleotide 313 binds to a plurality of second stranded nucleotides 314, 315, 315' to form the DNA scaffolding or multimer structure 312 as shown in FIG. 10. Each antibody species 301, 302 is bound to a respective DNA scaffolding 312, 322. DNA scaffolding 312 comprises repeating nucleic acid 315, 315' which each have a binding region that is hybridizable to nucleic acid 316, 316'. Nucleic acid 316, 316' are bound to enzyme 307, 307' using a spacer sequence 317, 317'. Similarly, DNA scaffolding 322 comprises repeating nucleic acid 323, 323' which each have a binding region that is hybridizable to nucleic acid 324, 324'. Nucleic acid 324, 324' are bound to enzyme 318, 318' using a spacer sequence 325, 325'. DNA scaffolding 322 also comprises nucleic acid 320 having a binding region for hybridizing with nucleic acid 319 that is covalently bound to species 301. In some embodiments, no spacer is used between the nucleic acid and enzyme. In other embodiments, additional spacers are provided between the repeating nucleic acid on each scaffolding 312 and 322.

Figure 11:
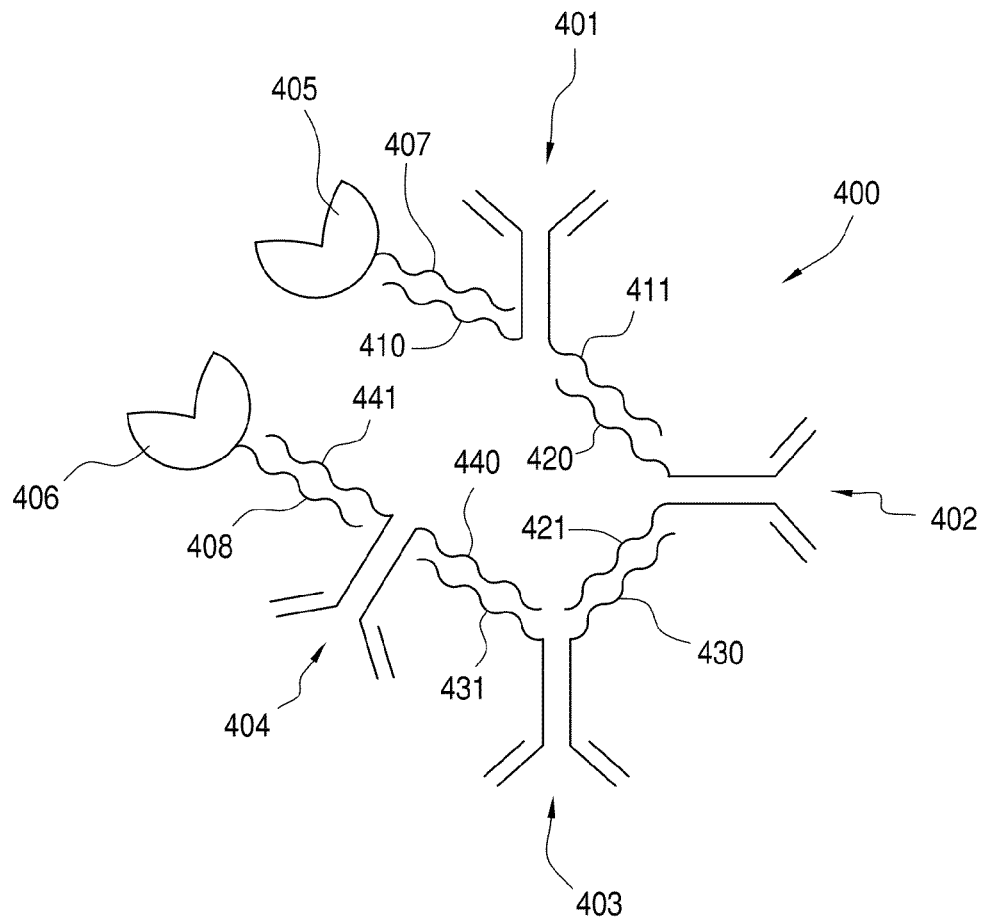
FIG. 11 is a representation of enzyme conjugate assembly according to an embodiment of the present invention.

FIG. 11 represents enzyme conjugate assembly 400 in according with one embodiment of the present invention. Enzyme conjugate assembly 400 comprises four antibodies 401, 402, 403 and 404, and two enzymes 405 and 406. Enzyme 405 has nucleic acid 407 bound thereto. Enzyme 406 has nucleic acid 408 bound thereto. For antibody 401, two different nucleic acid sequences, 410 and 411 are covalently bound. Antibody 402 has two nucleic acid sequences, 420 and 421 covalently bound. Antibody species 403 has two nucleic acid sequences, 430 and 431 covalently bound. Antibody species 404 has two nucleic acid sequences, 440 and 441 covalently bound. Nucleic acid sequence pairs form binding pairs as follows: 407 and 410, 411 and 420, 421 and 430, 431 and 440, and 441 and 408.

Figure 12:
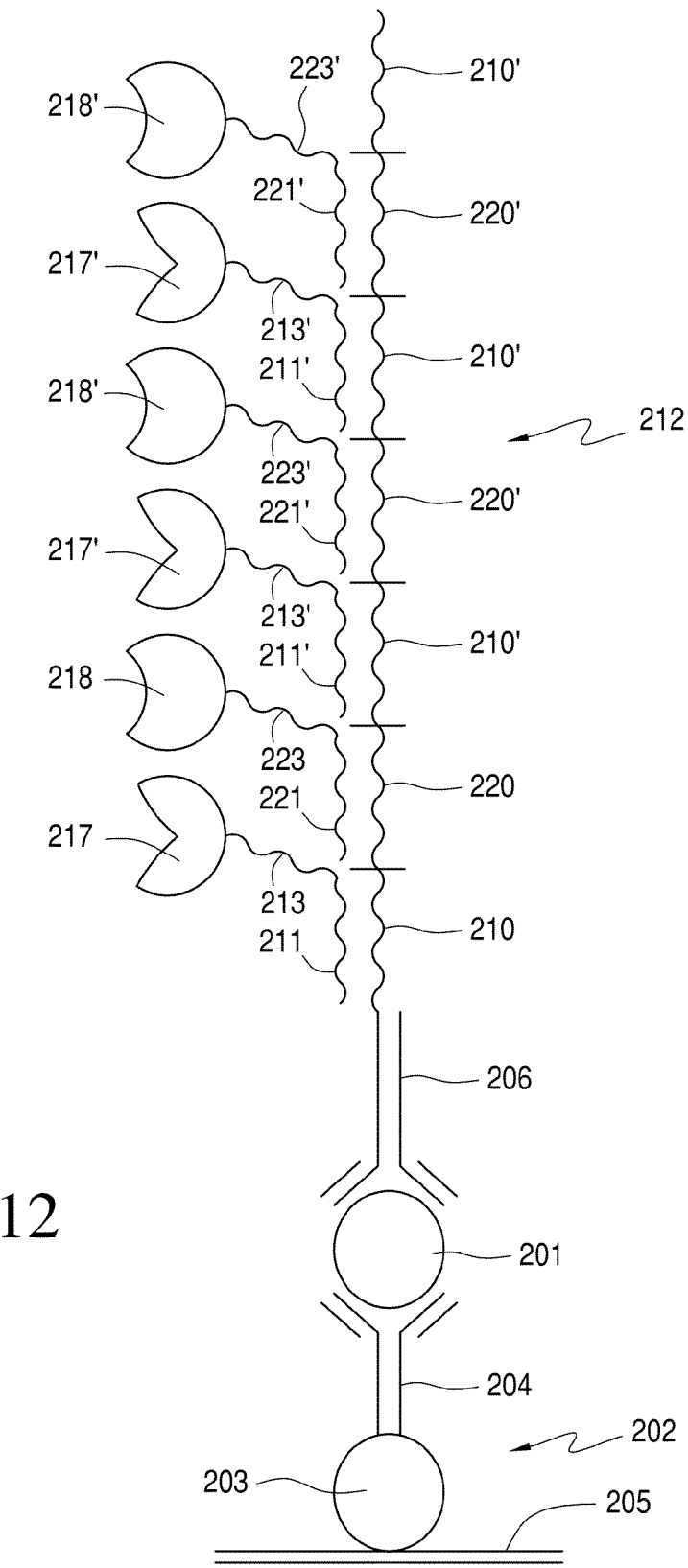
FIG. 12 is a representation of electrochemical detection of analyte using a polymer DNA scaffold to combine different enzyme species as a conjugate according to an embodiment of the present invention.

Returning to FIG. 6, there is shown one DNA scaffolding with multiple enzymes of the same type. In one embodiment, the DNA scaffolding may have different types of enzymes as shown in FIG. 12. In FIG. 12, capture bead 202 comprises carboxyl derivatized polystyrene bead 203 with a covalently attached capture antibody 204 on an electrode 205. During an analytical assay, an antigen 201 found in a test sample such as blood, where the antigen in this depiction is troponin cTnI, is bound by the capture antibody 204. A detection antibody, antibodies or binding fragment thereof 206 is conjugated to a nucleic acid sequence 210 that is part of DNA scaffolding 212 that is composed of alternate repeats of binding regions 210, 210' and 220, 220'. Two different nucleic acid conjugates are used in this analytic assay. A glucose oxidase enzyme 217, 217' conjugated to nucleic acid sequence 211, 211', with a spacer sequence 213, 213'. A horseradish peroxidase enzyme 218, 218' conjugated to nucleic acid sequence 221, 221' with a spacer sequence 223, 223'. Nucleic acid sequence 211, 211' binds to nucleic acid sequence 210, 210', respectively. Nucleic acid sequence 221, 221' binds to nucleic acid sequence 220, 220', respectively. In this analytical assay glucose is converted by glucose oxidase to hydrogen peroxidase. The hydrogen peroxidase in the presence of the substrate tetramethylbenzidine is converted to a blue color chemical species indicative of the signal.

Figure 13:
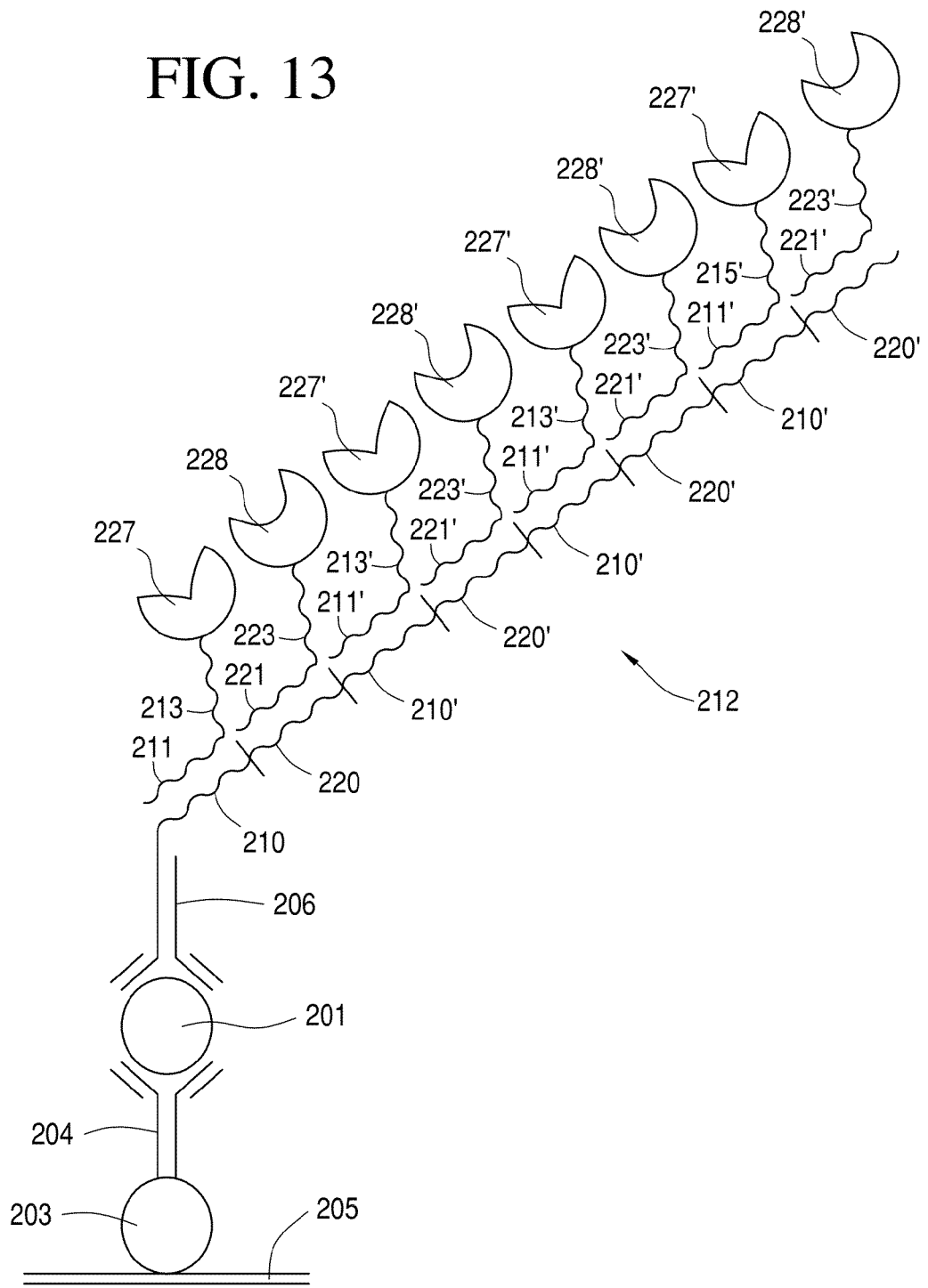
FIG. 13 is a representation of electrochemical detection of analyte using a polymer DNA scaffold to combine different enzyme species as a conjugate according to an embodiment of the present invention.

FIG. 13 depicts another DNA scaffolding 212 having different types of enzymes. D-lactate dehydrogenase [EC 1.1.2.7] 227, 227' is covalently bound to nucleic acid sequence 211, 211' using spacer sequence 213, 213'. Pyruvate oxidase [EC 1.2.3.3] 228, 228' is covalently bound to nucleic acid sequence 221, 221' using a spacer sequence 223, 223'. Nucleic acid sequences 211, 211' and 221, 221' bind to nucleic acid sequences 210, 210' and 220, 220', respectively. Lactate is converted to pyruvate by lactate dehydrogenase. The pyruvate is converted to hydrogen peroxide by pyruvate oxidase. The assembly of these components enables the electrogenic species hydrogen peroxide generated by the enzymes 227, 227' and 228, 228', to be in close proximity to the metal electrode 205, in turn generating an electrochemical signal.

Figure 14:
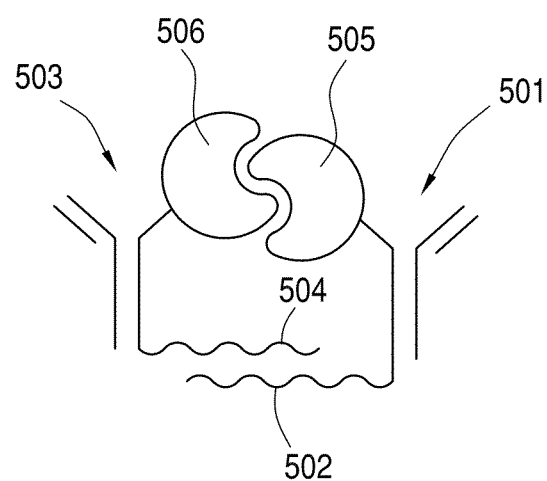
FIG. 14 is a representation of multiple antigen detection assays according to an embodiment of the present invention.

FIG. 14 represents a multiple antigen detection (MAD) assays. Such MAD assays are also described in US Pub. 2005/0095627, the entire contents and disclosure of which is hereby incorporated by reference. Antibody species 501 is covalently bound to nucleic acid 502. Antibody species 503 is covalently bound to nucleic acid 504. When antigen fragments or species 505 and 506 bind to each other and when antibodies 501 and 503 bind to their respective antigen fragments or species, 505 and 506, respectively, nucleic acid sequences 502 and 504 bind to each other in a complementary region.

FIGS. 15A-15D depicts the generation of a hybridization species dependent on antigen 603 binding to two antibodies 601, 602 at two different locations on an antigen 603. The nucleic acid hybridization is inefficient based on the region of hybridization and requires the increased thermodynamic stability of the antibody interaction. Antibody species 601 and 602 bind to antigen 603 at two different locations. Each antibody species 601 and 602 contain a heavy chain 604 and light chain 605. Antibody species 601 is covalently bound to nucleic acid sequence 606. Antibody species 602 is covalently bound to nucleic acid sequence 607. Nucleic acid sequence 606 is composed of a spacer region 610, binding region 611, binding region 612 and a DNA polymerization blocking nucleotide 613, such as a dideoxy or acyclonucleotide base. Nucleic acid sequence 607 is composed of a spacer region 615, binding region 616, binding region 617 and a DNA polymerization blocking nucleotide 618. The binding sequences 612 and 617 hybridize to each other. The spacer sequences 610 and 615 do not hybridize.

Figure 15A:
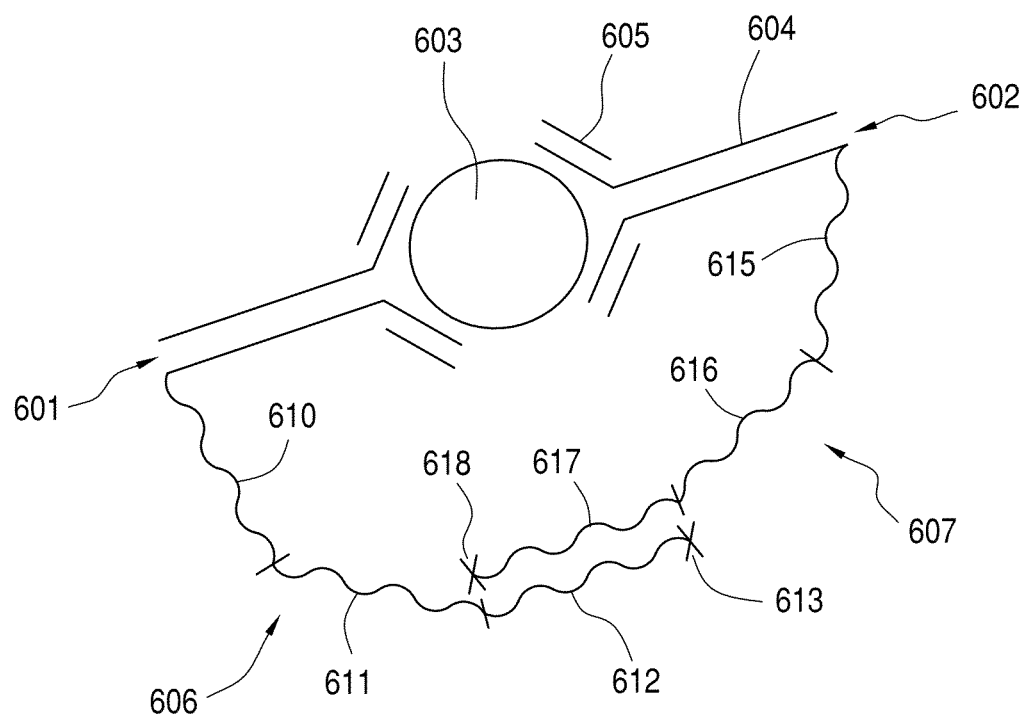
FIGS. 15A-15D represent of the generation of a hybridization species dependent on antigen binding according to an embodiment of the present invention.
Figure 15B:
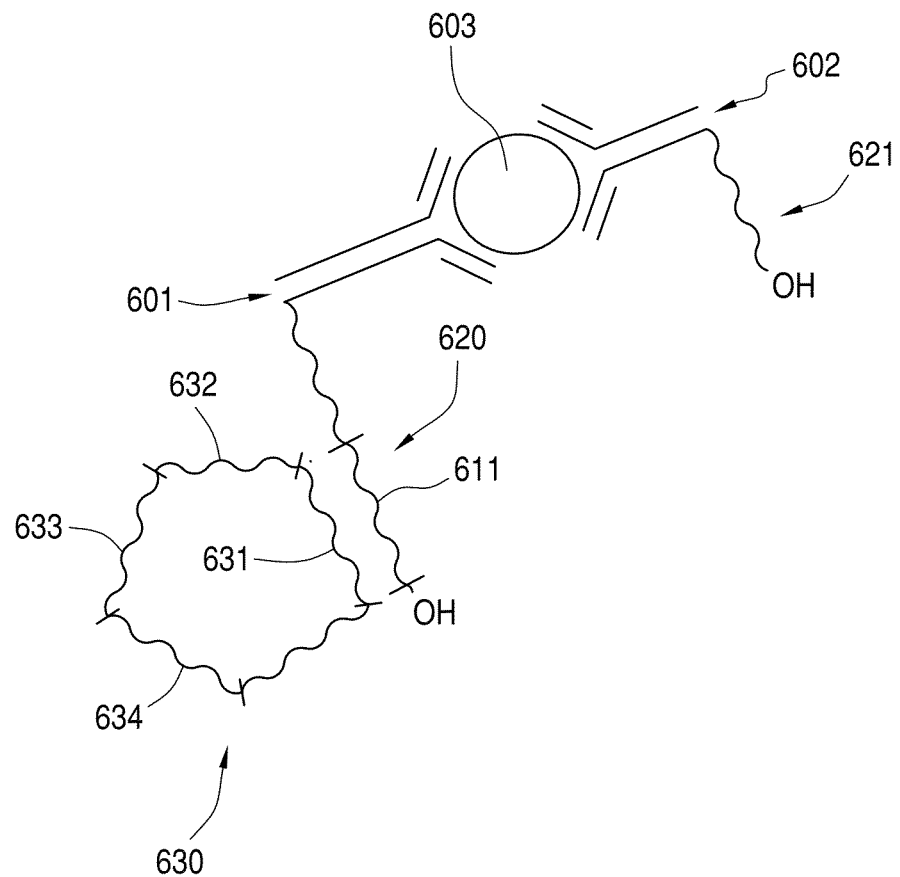

This structure of FIG. 15A is then treated with restriction endonuclease generating the structure shown in FIG. 15B. Antibody species 601 is covalently bound to nucleic acid 620 generated from the hybridization and enzymatic cleavage by restriction endonuclease from the original nucleic acid sequence 606. Antibody species 602 is covalently bound to nucleic acid sequence 621 generated from the hybridization and enzymatic cleavage by restriction endonuclease from the original nucleic acid sequence 607. Both nucleic acid sequences 620 and 621 contain a terminal 3' hydroxyl group. Nucleic acid structure 630 is a single stranded circular nucleic acid generated from either synthetic oligonucleotides circularized with Epicenter's CircLigase or single stranded phage or phagemid. Nucleic acid structure 630 contains the components of binding region 631 which hybridizes to 611, as well as binding regions 632, 633 and 634. The single stranded primer sequence 620 bound at binding region 611 with a free 3'-hydroxyl can use the circular structure 630 as a template for DNA synthesis by a strand displacing DNA polymerase and dNTPs. The ensuing structure is described in FIG. 15C.

Figure 15C:
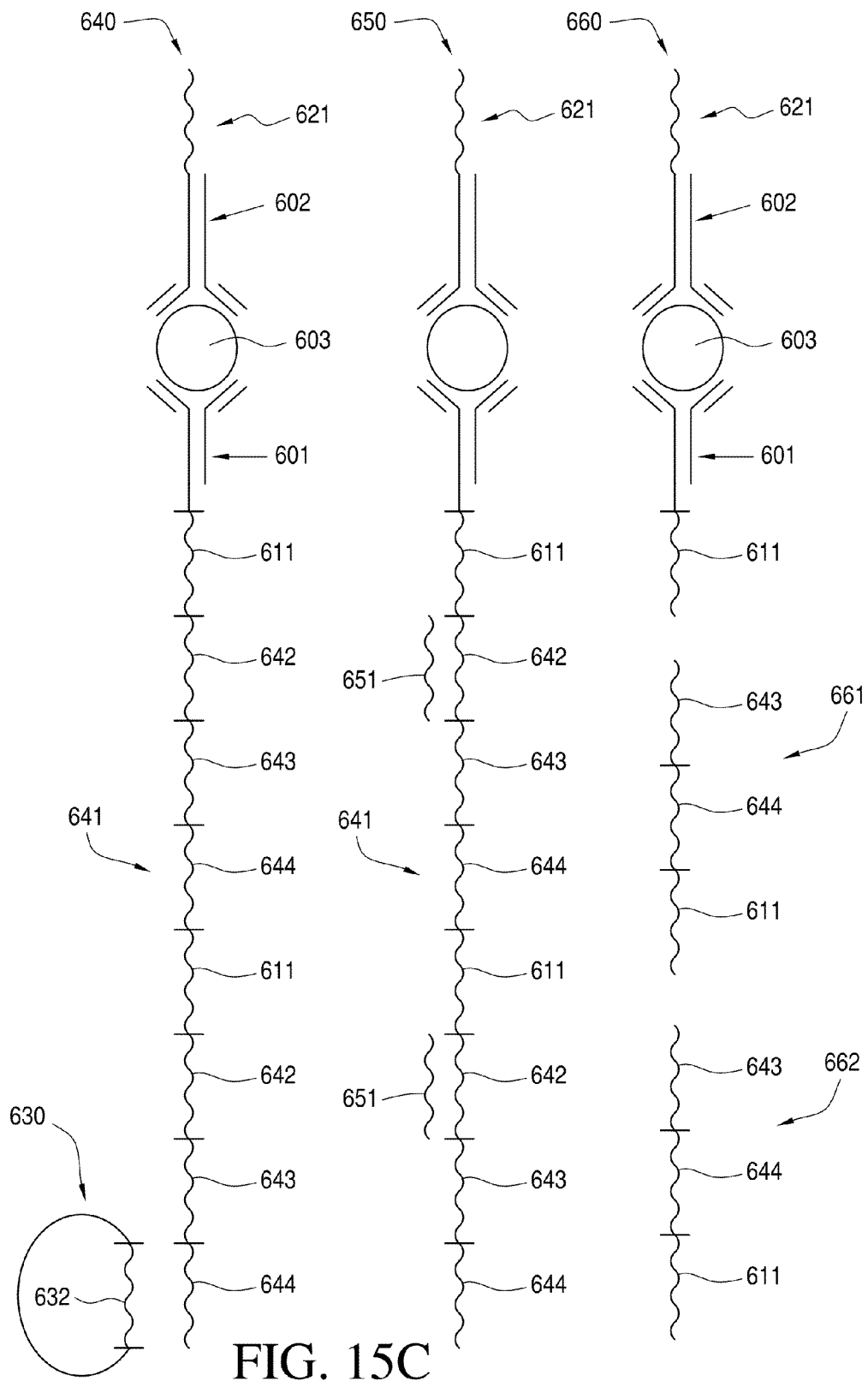

Structure 640 in FIG. 15C is composed of a nucleic acid sequence 621 covalently bound to antibody species 602, troponin antigen 603, antibody species 601 covalently bound to nucleic acid sequence 641. Nucleic acid sequence 641 is composed of repeating units of binding sequences 611, 642, 643 and 644. Binding region 632 from circular nucleic acid species 630 is hybridized at binding region 644.

Synthetic oligonucleotide sequences 651 which hybridize to binding sequence 642 are added to the reaction as depicted in structure 650. Restriction endonuclease is added to the reaction with structure 650 generating structure 660. The molecule will fragment into a molecule with nucleic acid sequence 621 and antibody species 602 covalently bound to each other, and the troponin antigen 603 bound to antibody species 602. The antigen 603 will also be bound to antibody species 601 which is covalently bound to nucleic acid sequence 611. Additional fragments 661 and 662 containing binding regions 643, 644 and 611 will be generated. These fragments 661, 662 are described in FIG. 15D in the analytical detection step.

Figure 15D:
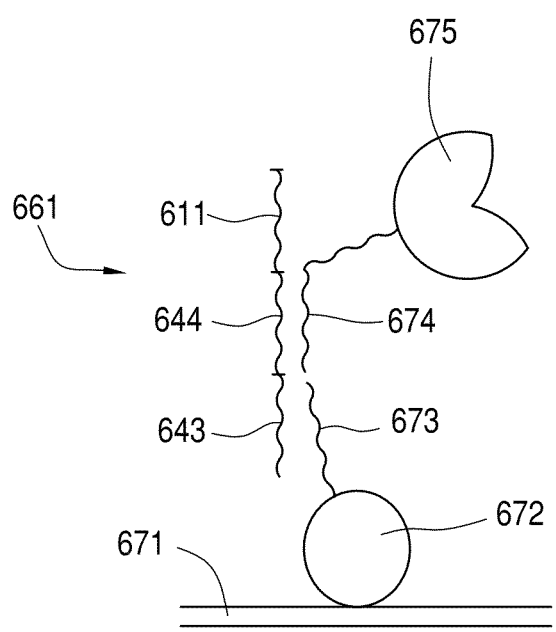

FIG. 15D depicts the detection step where the fragments 661 which has the subcomponent 643 which hybridizes to nucleic acid sequence 673 covalently attached to carboxyl polystyrene bead 672 which sits on top of a metal electrode 671. Fragment 661 also has a region 644 which hybridizes to nucleic acid sequence 674 which is covalently bound to alkaline phosphatase 675. The assembly of these components enables the electrogenic species generated by the enzyme 675 to be in close proximity to the metal electrode 671, in turn generating an electrochemical signal to be generated.

FIGS. 16A-16C depict an antigen analytical detection based on signal amplification from a nucleic acid strand displacement step. Starting with FIG. 16A, capture bead 703 is covalently bound to capture antibody 704. Antigen 701 is bound to antibody species 704. Nucleic Acid sequence 710 composed of binding sequences 711, 712 and 713, covalently bound to detecting antibody 706 is bound to antigen 701.

The sample is washed, followed by the addition of nucleic acid sequence 720 complementary to binding sequence 710, followed by DNA polymerization generating a newly synthesized sequence generating structure 715 as shown in FIG. 16B. Nucleic acid sequence 720 contains the binding components of 721, 722 and 723 hybridizable to binding components on nucleic acid sequence 710 designated 711, 712 and 713, respectively.

The strand displacement reaction generates nucleic acid sequence 725 containing the binding components 722 and 723 shown in FIG. 16C. The nucleic acid sequence 722 binds to complementary binding sequences 708 covalently bound to reacted carboxyl polystyrene beads 730 at a second capture site. The nucleic acid sequence 709 binds to the nucleic acid binding sequence 723 covalently and nucleic acid sequence 709 is bound to alkaline phosphate enzyme 707.

The assembly of these components enables the electrogenic species generated by the enzyme 707 described in the above '821 reference, to be in close proximity to the metal electrode (not shown), in turn generating an electrochemical signal to be generated.

It should be understood that the binding of the first and second stranded nucleotides replaces the crosslinker conventionally used to attach signal antibodies to signal elements. Thus, preferred embodiments of the invention do not require or employ a crosslinking agent and may be substantially or entirely free of such crosslinking agents.

Although antibodies are described above for binding with two epitopes of the analyte, in some embodiments, there may be three antibodies for binding with three epitopes of the analyte as described in U.S. Pub. No. 2004/0018577, the entirety of which is incorporated herein by reference. The analyte of interest and one or more subforms thereof may be detected by performing an immunoassay using antibodies specific for more than one epitope on the analyte either (i) on the capture side of the sandwich, (ii) signal side of the sandwich, (iii) or both. By targeting at least three epitopes, in total, on the analyte of interest, multiple sandwich assays of the present invention may detect the presence of the analyte and subforms thereof even if certain epitopes are unavailable for binding on the subform, so long as there is at least one epitope capable of binding by a capture antibody and at least one epitope available for binding by a signal antibody.

It should also be noted that FIGS. 1-16C, are for the purpose of conceptually representing the functionality of the various parts of the system. For example, an antibody molecule is drawn wherein the analyte binds to a pocket between the F(ab) molecules, whereas in the art it is known that the analyte would bind to the binding domain of the individual F(ab) fragments.

In immunosensor embodiments, it is advantageous to contact the sensor first with a sample and then with a wash fluid prior to recording a response from the sensor. Wash fluid may be used to remove the biological sample not bound to the electrode, i.e., the sample which is not of interest. In specific embodiments, the sample is amended with a signal conjugate (having the above described nucleotide linkage between signal antibody or antibodies and signal element(s)) that binds to the analyte of interest within the sample before the amended sample contacts the sensor. Binding reactions in the sample produce an analyte/signal conjugate complex. The sensor comprises an immobilized antibody to the analyte, attached close to an electrode surface. Upon contacting the sensor, the analyte/signal conjugate complex binds to the immobilized antibody near the electrode surface. It is advantageous at this point to remove from the vicinity of the electrode as much of the unbound antibodies as possible to minimize background signal from the sensor. Where the signal element comprises a signal enzyme such as ALP, the signal conjugate complex is advantageously capable of converting a substrate, provided in the fluid, to produce an electrochemically active species. This active species is produced close to the electrode and provides either a current from a redox reaction at the electrode when a suitable potential is applied (amperometric operation). Alternatively, if the electroactive species is an ion, it can be measured potentiometrically. In amperometric measurements the potential may either be fixed during the measurement, or varied according to a predetermined waveform. For example, a triangular wave can be used to sweep the potential between limits, as is used in the well-known technique of cyclic voltammetry. Alternatively, digital techniques such as square waves can be used to improve sensitivity in detection of the electroactive species adjacent to the electrode. From the current or voltage measurement, the amount or presence of the analyte in the sample is calculated. The signal is proportionate to the amount of the analyte of interest in the biological sample. These and other analytical electrochemical methods are well known in the art.

In embodiments in which the cartridge comprises an immunosensor, the immunosensor is advantageously microfabricated from a base sensor of an unreactive metal such as gold, platinum or iridium, and a porous permselective layer which is overlaid with a bioactive layer attached to a microparticle, for example latex particles. The microparticles are dispensed onto the porous layer covering the electrode surface, forming an adhered, porous bioactive layer. The bioactive layer has the property of binding specifically to the analyte of interest, or of manifesting a detectable change when the analyte is present, and is most preferably an immobilized antibody directed against the analyte.

Devices of the present invention include a cartridge, columns, syringe, cuvette, or other analytical device or system known in the art. The cartridge may be of a type as described in U.S. Pat. Nos. 7,419,821 and 5,096,669, the entireties of which are hereby incorporated by reference. Examples of other cartridge configurations are found in U.S. Pat. Nos. 5,416,026, 5,593,638, 5,447,440, 5,628,961, 5,514,253, 5,609,824, 5,605,664, 5,614,416, 5,789,253, 6,030,827, and 6,379,883, the entireties of which are incorporated herein by reference. Still other cartridge configurations are described in PCT/US00/31158, PCT/US01/04345, PCT/US2005/046772 and U.S. Publication Nos. 2007/0154922, 2005/0054078, 2004/0018577 and 2006/0160164, the entireties of which are incorporated herein by reference. In a preferred embodiment, a suitable cartridge may include i-STAT cTnl, manufactured by i-Stat, which may be used with the i-STAT Portable Clinical Analyzer, the i-STAT 1 Analyzer and the Philips Medical Systems Blood Analysis Module.

In an exemplary embodiment of the invention, there is provided a self-contained sensing device and reader. The self-contained sensing device may be disposable or a single use cartridge. The reader may be a hand-held reader having an output device such as a screen or printer. The operator, such as a physician, nurse or technician, places a sample to be tested in the sensing device and inserts the sensing device into the reader. Upon completion of the process, the operator removes the device from the reader and simply disposes of it. The reader is then ready to perform another measurement which is initiated by the insertion of another sensing device.

A suitable single-use cartridge comprises a housing having a sample entry port to receive the biological sample. The sample contains the target analyte, if present. The sample entry port is connected to a conduit having one or more electrodes. The electrodes have an attached capture antibody. The conduit preferably comprises the signal conjugate disposed between the entry port and the immobilized capture antibodies within a solubilizing agent, e.g., sugar matrix, as described above. The housing further comprises a region containing a wash fluid, a region containing an enzyme substrate (in embodiments where the signal element comprises a signal enzyme) and a waste chamber. The regions and waste chamber are connected to the conduit, such that the wash fluid may be transferred by pumping or suction from the region to the conduit to remove the biological sample from the conduit into the waste chamber. Also, in embodiments where the signal conjugate comprises a signal enzyme, the region containing the enzyme substrate is connected to the conduit such that the enzyme substrate may react with the signal enzyme that generates a signal at the electrode. In addition to these features the cartridge may contain one or more additional features as further described below.

Figure 17:
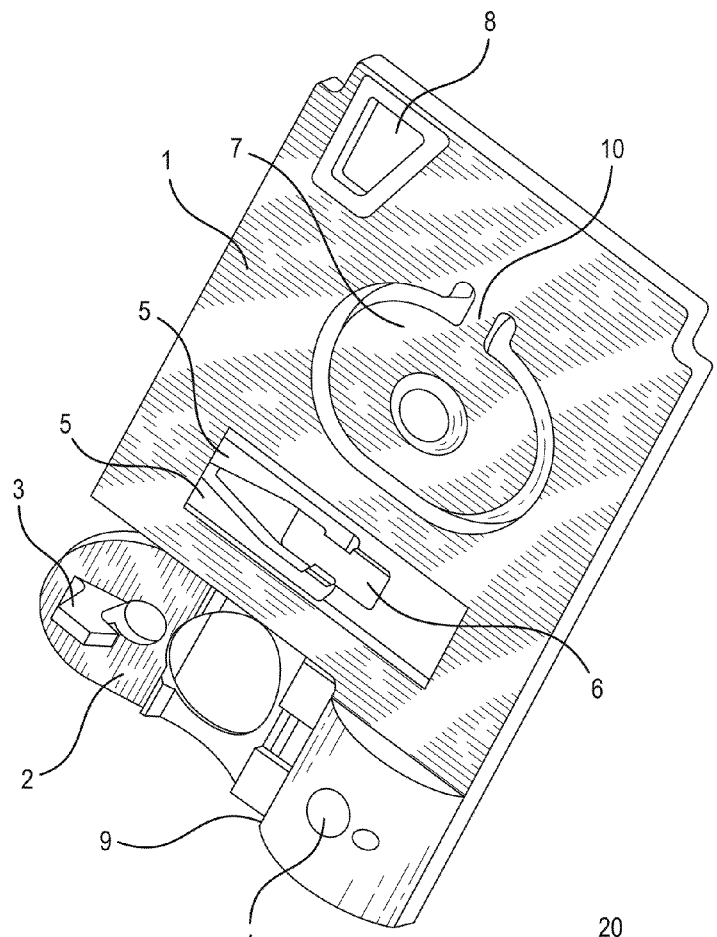
FIG. 17 is an isometric top view of an immunosensor cartridge cover.
Figure 18:
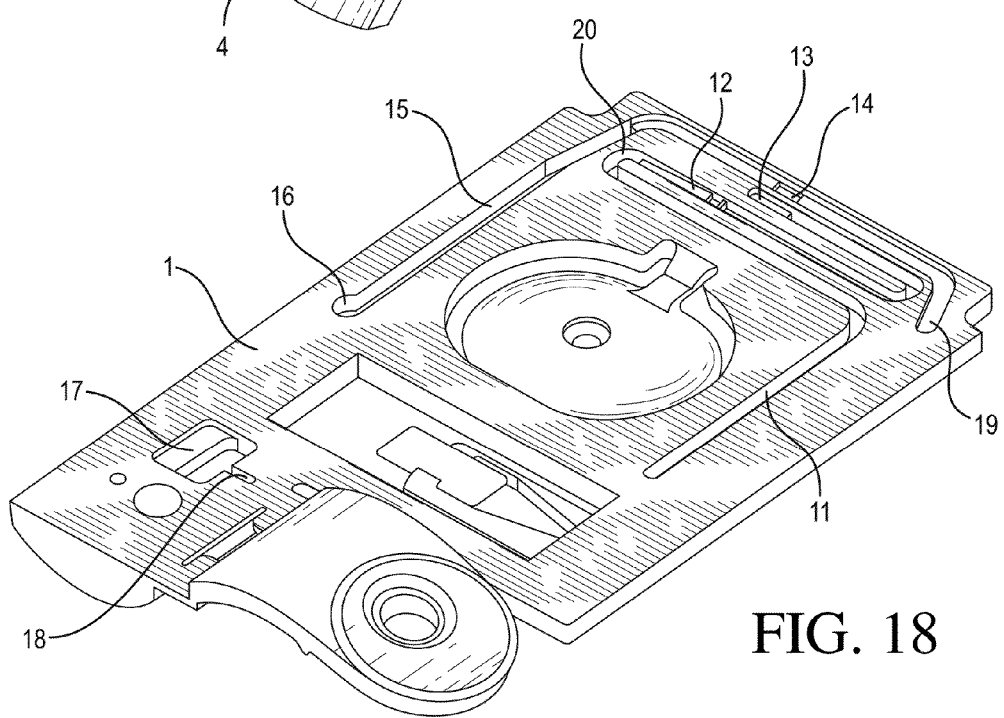
FIG. 18 is an isometric bottom view of an immunosensor cartridge cover.

The figures for the cartridge shown in FIGS. 17-22 and are also further described in U.S. Pat. No. 7,419,821 and U.S. Pub. Nos. 2006/0160164 and 2005/0054078, the entireties of which are incorporated herein by reference. In one embodiment, the sensing device may comprise a cartridge of the present invention. The cartridge comprises a cover as shown in FIGS. 17 and 18, a base shown in FIG. 20, and a thin-film adhesive gasket shown in FIG. 19, disposed between the base and the cover. Referring now to FIG. 17, the cover 1 is made of a rigid material, preferably plastic, capable of repetitive deformation at flexible hinge regions 5, 9, without cracking. The cover comprises a lid 2, attached to the main body of the cover by a flexible hinge 9. In operation, after introduction of a sample into the sample holding chamber 34, the lid can be secured over the entrance to the sample entry port 4, preventing sample leakage, and the lid is held in place by hook 3. In one embodiment, the cover comprises a slidable closure as described in U.S. Publication No. 2005/0054078, the entirety of which is incorporated herein by reference. The cover further comprises two paddles 6, 7, that are moveable relative to the body of the cover, and which are attached to it by flexible hinge regions 5, 10.

In operation, when operated upon by a pump means, paddle 6 exerts a force upon an air bladder comprised of cavity 43, which is covered by thin-film gasket 21, to displace fluids within conduits of the cartridge. When operated by a second pump means, paddle 7 exerts a force upon the gasket 21, which can deform because of slits 22 cut therein. The cartridge is adapted for insertion into a reading apparatus, and therefore has a plurality of mechanical and electrical connections for this purpose. It should also be apparent that manual operation of the cartridge is possible. Thus, upon insertion of the cartridge into a reading apparatus, the gasket transmits pressure onto a fluid-containing foil pack filled with approximately 130 μL of analysis/wash solution ("fluid") located in cavity 42, rupturing the package upon spike 38, and expelling fluid into conduit 39, which is connected via a short transecting conduit in the base to the sensor conduit. The analysis fluid fills the front of the analysis conduit first pushing fluid onto a small opening in the tape gasket that acts as a capillary stop. Other motions of the analyzer mechanism applied to the cartridge are used to inject one or more segments into the analysis fluid at controlled positions within the analysis conduit. These segments are used to help wash the sensor surface and the surrounding conduit with a minimum of fluid.

The cover further comprises a hole covered by a thin pliable film 8. In operation, pressure exerted upon the film expels one or more air segments into a conduit 20 through a small hole 28 in the gasket.

Referring to FIG. 18, the lower surface of the base further comprises second conduit 11, and first conduit 15. Second conduit 11 includes a constriction 12, which controls fluid flow by providing resistance to the flow of a fluid. Optional coatings 13, 14 provide hydrophobic surfaces, which together with gasket holes 31, 32, control fluid flow between conduits 11, 15. A recess 17 in the base provides a pathway for air in conduit 34 to pass to conduit 34 through hole 27 in the gasket.

Figure 19:
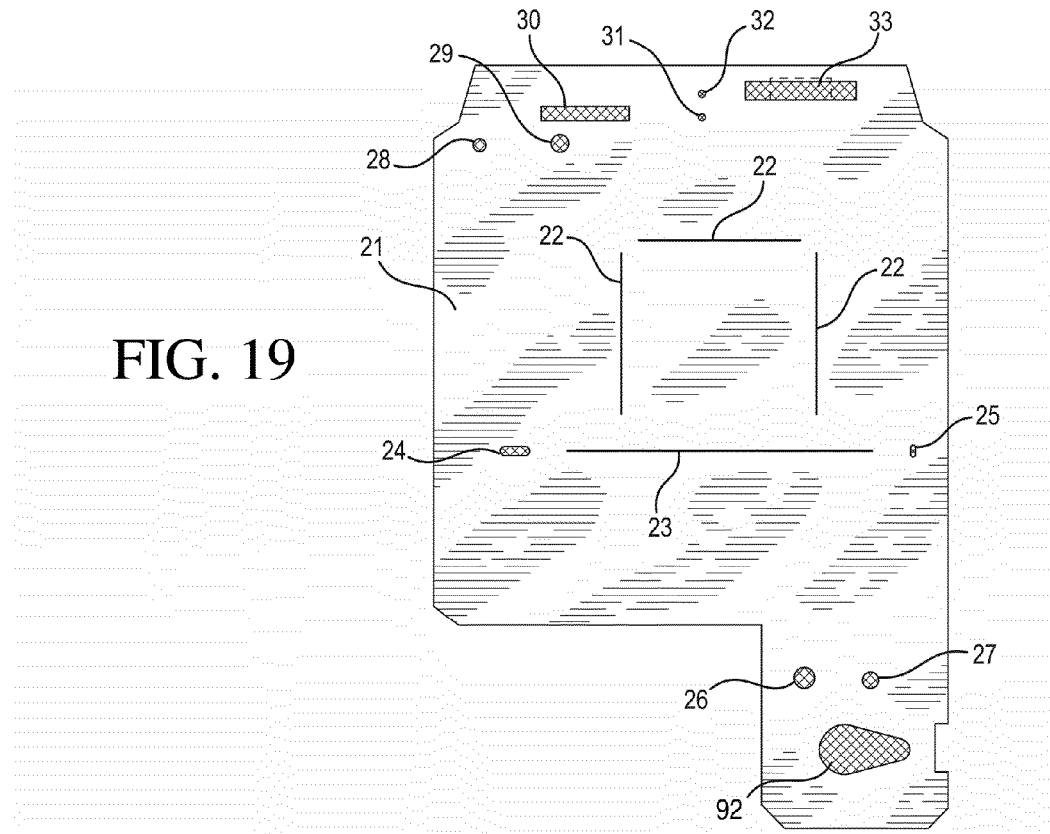
FIG. 19 is a top view of the layout of a tape gasket for an immunosensor cartridge.

Referring to FIG. 19, thin-film gasket 21 comprises various holes and slits to facilitate transfer of fluid between conduits within the base and the cover, and to allow the gasket to deform under pressure where necessary. Thus, hole 24 permits fluid to flow from conduit 11 into waste chamber 44; hole 25 comprises a capillary stop between conduits 34 and 11; hole 26 permits air to flow between recess 18 and conduit 40; hole 27 provides for air movement between recess 17 and conduit 34; and hole 28 permits fluid to flow from conduit 19 to waste chamber 44 via optional closeable valve 41. Holes 30 and 33 permit the plurality of electrodes that are housed within cutaways 35 and 37, respectively, to contact fluid within conduit 15. In a specific embodiment, cutaway 37 houses a ground electrode, and/or a counter-reference electrode, and cutaway 35 houses at least one analyte sensor and, optionally, a conductimetric sensor. Element 29 in FIG. 19 acts as an opening in the tape connecting a region in the cover FIG. 17 with the base FIG. 18. Hole 92 permits fluid to flow from entry port 4 to conduit 34.

Figure 20:
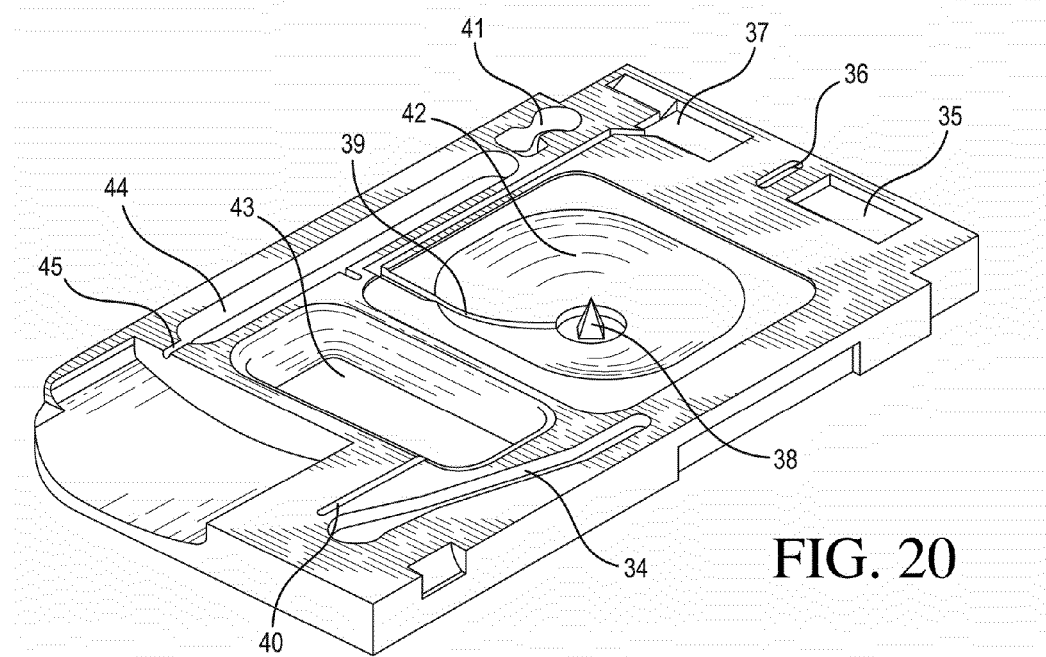
FIG. 20 is an isometric top view of an immunosensor cartridge base.

Referring to FIG. 20, conduit 34 is the sample holding chamber that connects the sample entry port 4 to first conduit 11 in the assembled cartridge. Cutaway 35 houses the analyte sensor or sensors, or an analyte responsive surface, together with an optional conductimetric sensor or sensors. Cutaway 37 houses a ground electrode if needed as a return current path for an electrochemical sensor, and may also house an optional conductimetric sensor. Cutaway 36 provides a fluid path between gasket holes 31 and 32 so that fluid can pass between the first and second conduits. Recess 42 houses a fluid-containing package, e.g., a rupturable pouch, in the assembled cartridge that is pierced by spike 38 because of pressure exerted upon paddle 7 upon insertion into a reading apparatus. Fluid from the pierced package flows into the second conduit at 39. An air bladder is comprised of recess 43 which is sealed on its upper surface by gasket 21. The air bladder is one embodiment of a pump means, and is actuated by pressure applied to paddle 6 which displaces air in conduit 40 and thereby displaces the sample from sample chamber 34 into first conduit 15.

The location at which air enters the sample chamber (gasket hole 27) from the bladder, and the capillary stop 25, together define a predetermined volume of the sample chamber. An amount of the sample corresponding to this volume is displaced into the first conduit when paddle 6 is depressed. This arrangement is therefore one possible embodiment of a metering means for delivering a metered amount of an unmetered sample into the conduits of the cartridge.

In the present cartridge, a means for metering a sample segment is provide in the base plastic part. The segment size is controlled by the size of the compartment in the base and the position of the capillary stop and air pipe holes in the tape gasket. This volume can be readily varied from 2 to 200 microliters. Expansion of this range of sample sizes is possible within the context of the present invention.

The fluid is pushed through a pre-analytical conduit 11 that can be used to amend a reagent (e.g. particles or soluble molecules) into the sample prior to its presentation at the sensor conduit 19. Alternatively, the amending reagent may be located in portion 15, beyond portion 16. Pushing the sample through the pre-analytical conduit also serves to introduce tension into the diaphragm pump paddle 7 which improves its responsiveness for actuation of fluid displacement.

In some assays, metering is advantageous if quantification of the analyte is required. A waste chamber is provided, 44, for sample and/or fluid that is expelled from the conduit, to prevent contamination of the outside surfaces of the cartridge. A vent connecting the waste chamber to the external atmosphere is also provided, 45. A feature of the cartridge is that once a sample is loaded, analysis can be completed and the cartridge discarded without the operator or others contacting the sample.

Figure 21:
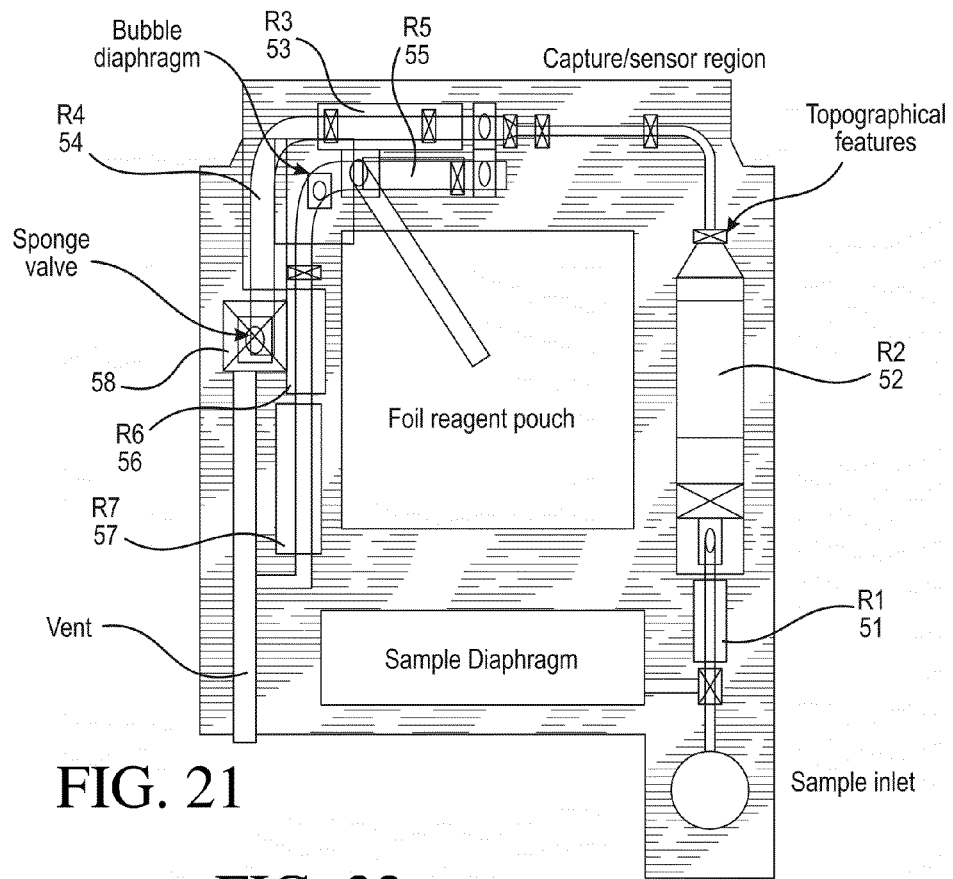
FIG. 21 is a schematic view of the layout of an immunosensor cartridge.

Referring now to FIG. 21, a schematic diagram of the features of a cartridge and components is provided, wherein 51-57 are portions of the conduits and sample chamber that can optionally be coated with dry reagents, such as the signal conjugates, optionally in a solubilizing agent, to amend the sample or fluid. The sample or fluid is passed at least once over the dry reagent to dissolve it. Reagents used to amend samples or fluid within the cartridge include signal conjugates, or blocking agents that prevent either specific or non-specific binding reactions among assay compounds. A surface coating that is not soluble but helps prevent non-specific adsorption of assay components to the inner surfaces of the cartridges can also be provided.

Within a segment of sample or fluid, an amending substance can be preferentially dissolved and concentrated within a predetermined region of the segment. This is achieved through control of the position and movement of the segment. Thus, for example, if only a portion of a segment, such as the leading edge, is reciprocated over the amended substance, then a high local concentration of the substance can be achieved close to the leading edge. Alternatively, if an homogenous distribution of the substance is desired, for example if a known concentration of an amending substance is required for a quantitative analysis, then further reciprocation of the sample or fluid will result in mixing and an even distribution.

In specific embodiments, a closeable valve is provided between the first conduit and the waste chamber. In one embodiment, this valve, 58, is comprised of a dried sponge material that is coated with an impermeable substance. In operation, contacting the sponge material with the sample or a fluid results in swelling of the sponge to fill the cavity 41, thereby substantially blocking further flow of liquid into the waste chamber 44. Furthermore, the wetted valve also blocks the flow of air between the first conduit and the waste chamber, which permits the first pump means connected to the sample chamber to displace fluid within the second conduit, and to displace fluid from the second conduit into the first conduit in the following manner. After the sample is exposed to the sensor for a controlled time, the sample is moved into the post-analytical conduit 19 where it can be amended with another reagent. It can then be moved back to the sensor and a second reaction period can begin. Alternately, the post-analysis conduit can serve simply to separate the sample segment from the sensor. Within this post-analysis conduit is a single closeable valve which connects the air vent of the sensor conduit to the diaphragm air pump. When this valve closes, the sample is locked in the post analytical conduit and cannot be moved back to the sensor chip. There are several different design examples for this valve that are encompassed within the present invention. Some designs are activated mechanically while others activate on liquid contact. Other types of closeable valve that are encompassed by the present invention include, but are not limited to; a flexible flap held in an open position by a soluble glue or a gelling polymer that dissolves or swells upon contact with a fluid or sample thus causing the flap to close; and alternatively, in one specific embodiment, a thin layer of a porous paper or similar material interposed between a conduit and either the waste chamber or ambient air such that the paper is permeable to air while dry but impermeable when wet. In the latter case it is not necessary that the closeable valve be interposed between a conduit and the waste chamber: the valve passes little to no liquid before closing and so the valve is appropriately placed when positioned between a conduit and the ambient air surrounding the cartridge. In practical construction, a piece of filter paper is placed on an opening in the tape gasket in the fluid path to be controlled. Air can readily move through this media to allow fluid to be moved through the fluid path. When the fluid is pushed over this filter, the filter media becomes filled with liquid and further motion through the fluid path is stopped. Once the filter become wet, significant pressures would be required to move liquid through the pores of the filter. Air flow through the filter is also prevented because of the higher pressure required to push the liquid out of the filter. This valve embodiment requires very little liquid to actuate the valve, and actuation occurs rapidly and reliably. Materials, their dimensions, porosity, wettability, swelling characteristics and related parameters are selected to provide for rapid closure, within one second or more slowly, e.g. up to 60 seconds, after first contacting the sample, depending on the specific desired closure time.

Alternatively, the closeable valve is a mechanical valve. In this embodiment, a latex diaphragm is placed in the bottom of the air bladder on top of a specially constructed well. The well contains two openings which fluidically connect the air vent to the sample conduit. As the analyzer plunger pushes to the bottom of the air bladder, it presses on this latex diaphragm which is adhesive backed and seals the connection between the two holes. This blocks the sample's air vent, locking the sample in place.

Figure 22:
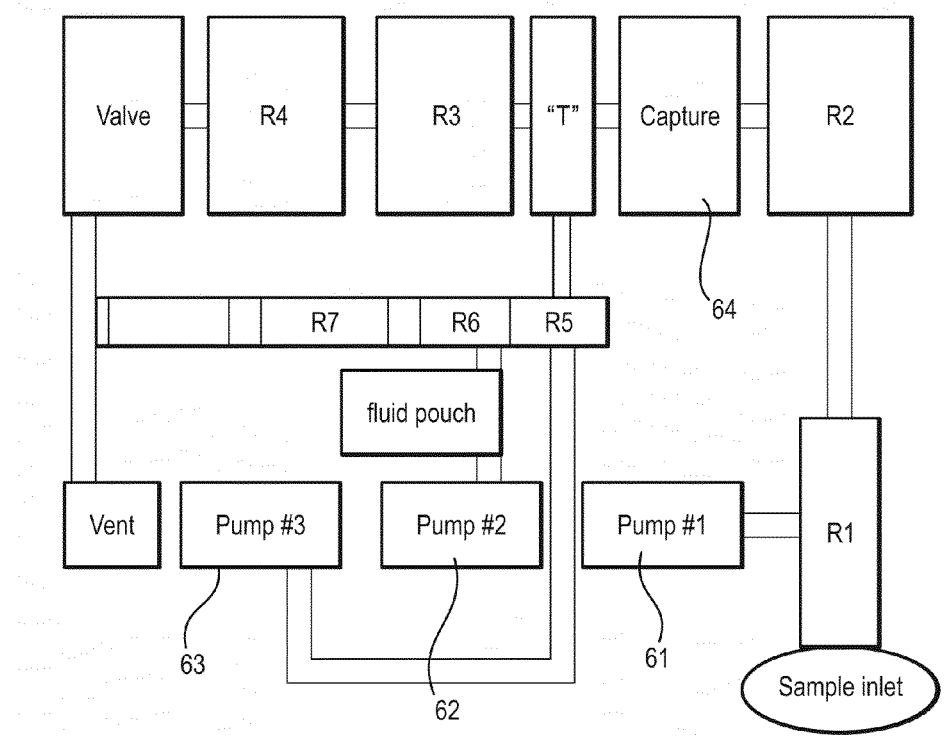
FIG. 22 is a schematic view of the fluid and air paths within an immunosensor cartridge, including sites for amending fluids with dry reagents.

Referring now to FIG. 22, which illustrates the schematic layout of an immunosensor cartridge, there are provided three pump means, 61-63. While these pumps have been described in terms of specific embodiments, it will be readily understood that any pump means capable of performing the respective functions of pump means 61-63 may be used within the present invention. Thus, pump means 1, 61, must be capable of displacing the sample from the sample holding chamber into the first conduit; pump means 2, 62, must be capable of displacing fluid within the second conduit; and pump means 3, 63, must be capable of inserting at least one segment into the second conduit. Other types of pump which are envisaged in the present application include, but are not limited to, an air sac contacting a pneumatic means whereby pressure is applied to said air sac, a flexible diaphragm, a piston and cylinder, an electrodynamic pump, and a sonic pump. With reference to pump means 3, 63, the term "pump means" includes all methods by which one or more segments are inserted into the second conduit, such as a pneumatic means for displacing air from an air sac, a dry chemical that produces a gas when dissolved, or a plurality of electrolysis electrodes operably connected to a current source. In a specific embodiment, the segment is produced using a mechanical segment generating diaphragm that may have more than one air bladder or chamber. The well 8 has a single opening which connects the inner diaphragm pump and the fluid filled conduit into which a segment is to be injected 20. The diaphragm can be segmented to produce multiple segments, each injected in a specific location within a fluid filled conduit.

In alternative embodiments, a segment is injected using a passive feature. A well in the base of the cartridge is sealed by tape gasket. The tape gasket covering the well has two small holes on either end. One hole is open while the other is covered with a filter material which wets upon contact with a fluid. The well is filled with a loose hydrophilic material such as a cellulose fiber filter, paper filter or glass fiber filter. This hydrophilic material draws the liquid into the well in the base via capillary action, displacing the air which was formerly in the well. The air is expelled through the opening in the tape gasket creating a segment whose volume is determined by the volume of the well and the volume of the loose hydrophilic material. The filter used to cover one of the inlets to the well in the base can be chosen to meter the rate at which the fluid fills the well and thereby control the rate at which the segment is injected into the conduit in the cover. This passive feature permits any number of controlled segments to be injected at specific locations within a fluid path and requires a minimum of space.

Embodiments of the present invention may also use employ techniques for correcting the signal. Suitable techniques are described in U.S. Patent No. 2006/0160164, the entirety of which is incorporated herein by reference.

While use of the embodiments is particularly advantageous in the medical environment and will be described in that context, it will be appreciated that the embodiments may be practiced in any situation where it is desired to perform chemical analyses of fluid samples at speeds which approach real-time. For example such embodied methods and device may be used to determine whether a patient may suffer a myocardial infarction or whether a patient has suffered a myocardial infarction.

The present invention will be better understood by the following non-limiting Examples.

EXAMPLE 1

The first example is an enzyme-linked immunoassay (ELISA) based on synthetic oligonucleotides to bridge a detection antibody and ALP enzyme as a conjugate for the analyte, as shown in FIG. 5.

This example demonstrates the basic concept of this system, wherein an ALP enzyme molecule uses a DNA scaffold to bind to a detection Ab or reduced F(ab) molecule, for use in an ELISA test. More complicated scaffolding molecules can be developed from this concept system.

The synthetic oligonucleotide sequences A and A' are preferably those shown below.

```
A (DE)
                                                       (SEQ ID NO: 1)
5'-amino C12-(T)20-TGATCGCTACGGTGGTATTGT-3' 6-FAM where FAM is a fluorescent label A' (AP)
                                                       (SEQ ID NO: 2)
5'-thiol modifier C6 S-S-(T)20-ACAATACCACCGTAGCGATC*A-3'6FAM where FAM is a fluorescent label
*denotes phosphorothioate linkage
(T)20 denotes 20 'T' residues
```

In order to demonstrate the entire system, the individual components were generated and tested for their functionality, as described below.

A set of experiments were performed to demonstrate the generation of an ALP-A' DNA protein conjugate as follows. Synthetic Oligonucleotide Beads:

As a test system for the ALP-DNA conjugate described below, beads were generated with attached complementary synthetic oligonucleotide sequences.

Twenty μL of 0.33 um carboxylate beads (2% solids final) (Bangs Lab) were transferred to a silanized 0.5 mL microcentrifuge tube. This was microcentrifuged at 12500 RPM for 1 min, the tube was rotated 180 degrees, then further microcentrifuged for an additional 4 minutes. The supernatant was removed, and 95 μL 100 mM MES (2-(N-morpholino) ethanesulfonic acid), pH 7.1 was added. The beads were microcentrifuged as above, and supernatant removed. Next 7.5 mg of EDAC (1-ethyl-3-(3-dimethylaminopropyl) carbodiimide hydrochloride) was added to 300 μL of MES buffer, pH 7.1. EDAC is a carboxyl group activator to couple amine groups. The first step in this process is that the carboxyl group is activated to an o-acylisourea group which can then react with an available amine group, which was synthesized into the synthetic oligonucleotide (A), forming a covalent attachment of the synthetic oligonucleotide to the carboxy group on the carboxyl beads. This was added to the beads and the solution was vortexed to mix well. The beads were then sonicated for 10 minutes in a sonication bath. The beads were pelleted by microcentrifugation as described above, and the supernatant was removed. Next 288 μL of MES, pH 7.1 was added and mixed by pipetting. Twelve μL of 100 uM amine modified oligonucleotide was added to the tube. The solution was vortexed to mix well. The solution was then sonicated for 10 minutes in a sonication bath. Then the tube was allowed to mix for 2 hours at room temperature in an incubator. The beads were concentrated by microcentrifugation as described above. Ninety five μL of quench buffer (50 mM MES, pH 7.1, 35 mM glycine, 0.25% BSA, 0.05% Tween-20, 0.05% NaN$_3$) was added and the solution mixed by pipetting. This buffer is added as glycine contains an amine group which will react with any uncoupled EDAC activated carboxy groups, blocking the EDAC activated carboxy groups, preventing further cross coupling in the reaction. The tube was mixed on a Clay Adams™ nutator (Becton Dickinson, Franklin Lakes, N.J.) to provide continuous mixing in multiple directions for 30 minutes at room temperature. The beads were pelleted as described above. Ninety five μL of storage buffer (50 mM MES, pH 7.1, 0.05% BSA, 0.05% $NaN_3$) was added and the beads were mixed by pipetting. The tubes were covered with parafilm to avoid drying, and then stored at −80° C. for long term storage (or at 4° C. for short term storage).

When prepared for microdispensing on bio sensor electrodes, the tubes were thawed then the beads were pelleted by microcentrifugation as described above. Ninety five μL of autoclaved deionized water was added, and the beads mixed by pipetting. These beads were then microdispensed on biosensor electrodes, e.g., the Pt and Au metal electrode surface shown in FIG. 5.

Reference beads, used as a background signal detector are further described in U.S. Pub. No. 2006/0160164, the entire contents and disclosures of which are hereby incorporated by reference. The reference beads are prepared for the microdispense.

Synthetic Oligonucleotide Processing:

For the protein-DNA conjugation the thiol modified synthetic oligonucleotide are treated with a mercaptan (DTT) to generate a free sulfhydryl group which can subsequently react with the 2-pyridyldithio group of LC-SPDP (succinimidyl 6-[3'-(2-pyridyldithio)-propionamido) hexanoate crosslinker attached to the protein's amine group via its N-hydroxysuccinimide (NHS) ester group.

It should be noted that this procedure is typically performed in as short a period of time, as possible. As this synthetic oligonucleotide contains a fluorescent tag, the reaction and columns are performed under aluminum foil or in a darkened room. Approximately 50,000 pmols of A' synthetic oligonucleotide is resuspended in 10 μL of 1×PBSE (136 mM NaCl, 2.7 mM KCl, 10.1 mM $Na_2HPO_4$, 1.8 mM $KH_2PO_4$, 5 mM EDTA Ethylenediaminetetraacetic acid), pH 7.4) and 20 μL of 1M DTT (dithiothreitol) in autoclaved deionized water is added. The reaction is allowed to proceed for 15 minutes at room temperature. Once this reaction is complete, 50 μL of 1×PBSE is added, and the entire reaction is loaded onto a size exclusion column.

As the unreacted DTT will interfere with subsequent steps, it is removed using size exclusion chromatography.

Figure 23:
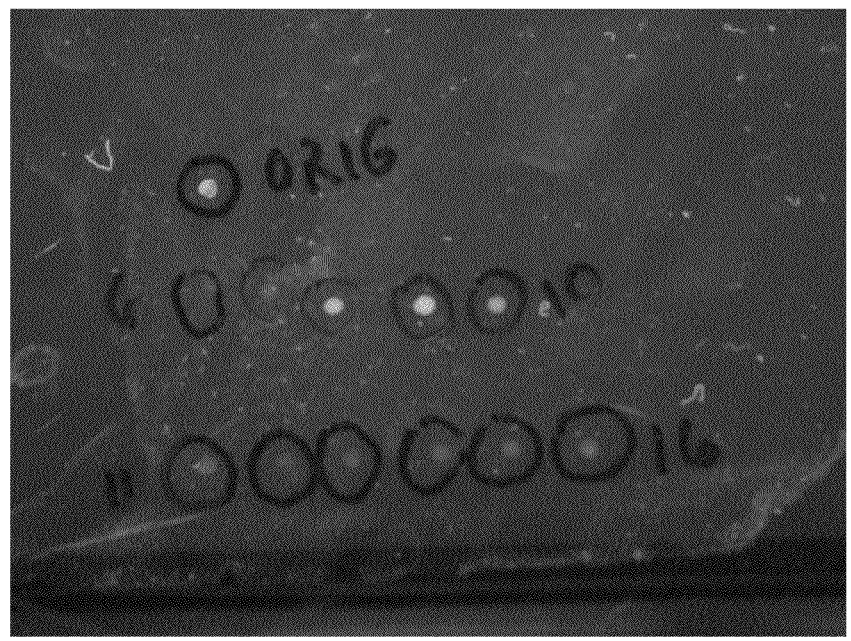
FIG. 23: fluorescing fractions from size exclusion column in accordance with an embodiment of the present invention.

A P-6 (Bio-Rad) size exclusion column is prepared using a 5 mL plastic pipette cut off at the '0' (mL) mark, siliconized glass wool is placed into the tip of the pipette and the P-6 slurry pre-swelled in autoclaved deionized water is added until the column resin fills to the '1' (mL) mark. The column is rinsed with 5 mL of autoclaved deionized water. To this column the DTT treated synthetic oligonucleotide is loaded. Fourteen 200 μL fractions were collected in separate microcentrifuge tubes using water as buffer. The fractions containing synthetic oligonucleotide were determined by the characteristic yellow color. Additionally, 1 μL samples were taken from each fraction and spotted onto saran wrap placed on top of a UV transilluminator. The brightly fluorescing spots contained synthetic oligonucleotide with associated fluorescent moieties, as shown in FIG. 23.

In a size exclusion column, larger molecules (synthetic oligonucleotides) elute earlier than smaller molecules (DTT). The DTT being a smaller molecule elute in fractions not found with the fluorescently labeled synthetic oligonucleotide. The yellow color and fluorescing fractions confirm the presence of the synthetic oligonucleotide which contains a 6-FAM (6-carboxyfluorescein) fluorescent dye covalently attached to the synthetic oligonucleotide.

The fractions containing fluorescing material (FIG. 23) were combined and dried in a vacuum centrifuge at 60° C. in the dark.

ALP Enzyme Processing:

While processing the sulfhydryl containing oligonucleotide, the LC-SPDP crosslinker's N-hydroxysuccinimide (NHS) ester moiety is reacted with the amine groups present on the protein molecule, forming a covalent attachment of the crosslinker to the protein, leaving an exposed 2-pyridyldithio group which will be used later to react with the DTT reacted synthetic oligonucleotide.

Figure 24:
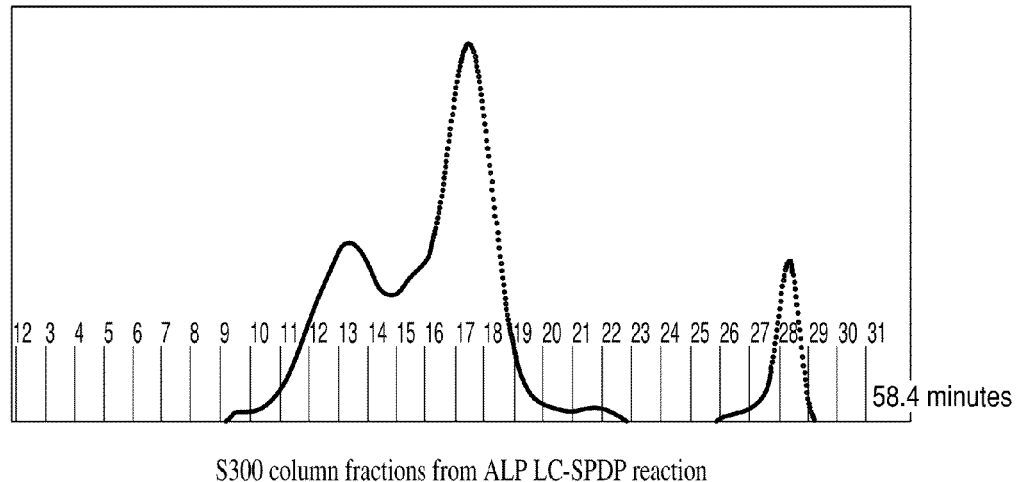
FIG. 24: S300 column fractions from ALP LC-SPDP reaction.

A 20 mM solution of LC-SPDP (Pierce) in N,N-dimethylformamide was prepared and 5 μL was added to 1 mg of Calf Intestinal Alkaline Phosphatase [E.C. 3.1.3.1] (ALP) enzyme made up to 100 μL in 1×PBSE. This reaction was allowed to proceed for 1 hour at room temperature with shaking. This material was loaded onto an S-300 size exclusion column attached to an AKTAprime plus (Amersham Biosciences) using PrimeView software for data collection. The unreacted LC-SPDP crosslinker is removed from the reacted protein sample to avoid contaminating reactions with the unreacted cross-linker and the synthetic oligonucleotide added in the next step of the process which should react with the activated protein molecule and not the unreacted cross-linker. 1/5× PBSE (27.2 mM NaCl, 0.54 mM KCl, 2 mM Na2HPO4, 0.4 mM KH2PO4, 5 mM EDTA, pH 7.4) was used as the buffer. The column was processed at 2 mL/min with 30 fractions of 4 mL, as shown in FIG. 24.

The resulting column data was displayed using software to associate fraction numbers to absorbance.

In this example fractions from 11 to 14 and 15 to 18 were combined individually. The fractions were concentrated to about 200-300 μL by centrifuging the samples in ULTRA-15 MWCO diafiltration columns (Amicon) for 35 minutes at 4,000 RPM.

To confirm the enzyme active fraction, 1 μL of each fraction was added to 1.2M diethanolamine, 0.5 mM $MgCl_2$, 19 mM 4-nitrophenol phosphate. The active enzyme fraction (fractions 15 to 18) turned yellow within 5 minutes, indicative of ALP enzyme activity, and was used for subsequent processing.

The concentrated fractions 15 to 18 containing active enzyme activity and anticipated to contain significant LC-SPDP conjugated protein was added directly to the dried DTT-treated synthetic oligonucleotide. Using dried synthetic oligonucleotide helps increase the concentration of the reactants. As described above, the covalently attached LC-SPDP crosslinker's 2-pyrdyldithio group will react with the sulthydryl group on the DTT treated synthetic oligonucleotide. The solution was gently pipetted to assure adequate dissolution of the dried synthetic oligonucleotide. It was allowed to react overnight at 4° C. with shaking.

Figure 25:
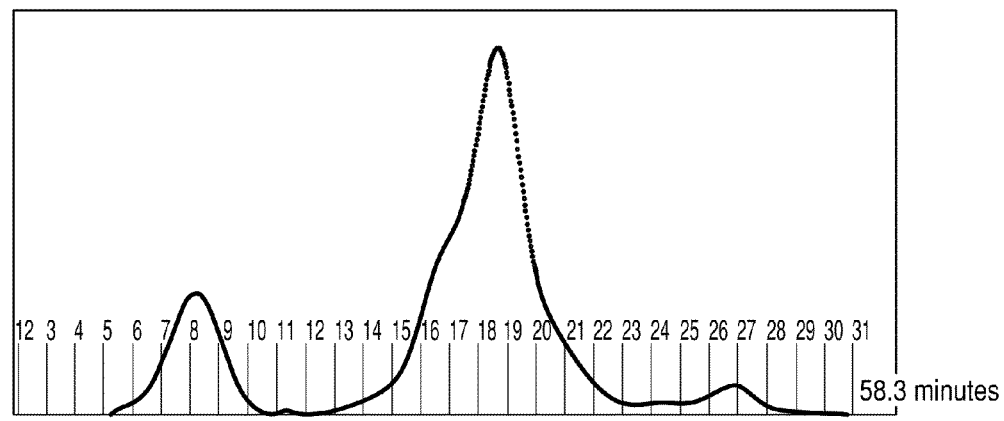
FIG. 25: S300 column fractions from ALP LC-SPDP reacted with DTT-treated synthetic oligonucleotide.

The LC-SPDP activated ALP reacted with DTT-treated synthetic oligonucleotide was then loaded onto an S300 column and processed as described above, as shown in FIG. 25.

The major peak from fractions 15 to 21 was combined and concentrated by diafiltration as described above. The material was stored in aluminum foil at 4° C.

Figure 26:
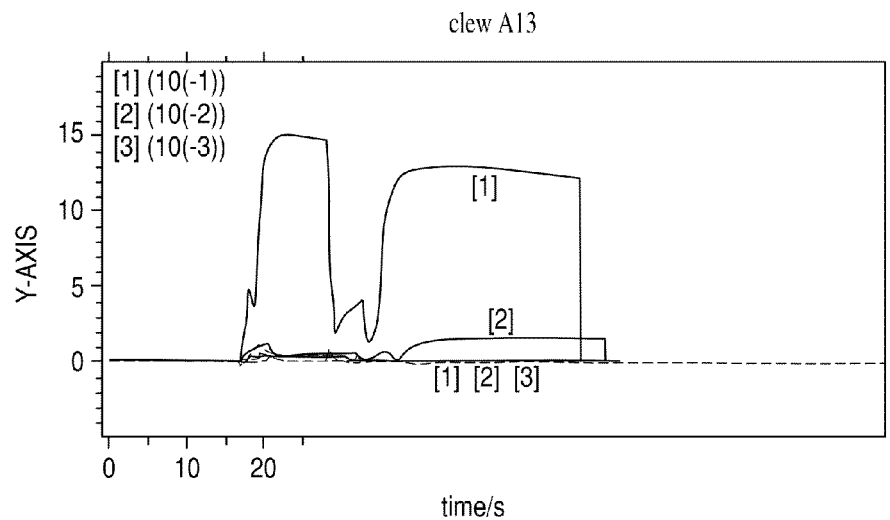
FIG. 26: Chronoamperometric plot of three dilutions (10-1 (37.3 ng), 10-2 (3.73 ng), 10-3 (0.37 ng) of ALP-A' conjugate tested in 'A' containing i-STAT 'immuno' cartridges using WinISD software.

This material was tested to confirm the attachment of the A' synthetic oligonucleotide. A dilution series of this material was generated. Two μL of this material was added to 18 μL of 1×PBSE (10-1), 2 μL of 10-1 was added to 18 μL of 1×PBSE (10-2), and 2 μL of 10-2 was added to 1×PBSE (10-3). Two μL of each of these dilutions was added to 18 μL of plasma and tested in a modified i-STAT "immuno" cartridge containing a bead with bound A synthetic oligonucleotide (described above). The cartridge is the same as the commercial cTnI device with the exception of the beads immobilized on the electrode, which have a synthetic DNA oligonucleotide attached to the bead and the ALP enzyme activity is supplied by the DNA conjugated to the ALP molecule. The presence of ALP with A' synthetic oligonucleotide which binds to the A sequence on the bead in the presence of an electrogenic substrate (p-aminophenol phosphate) after ALP cleavage generates an amperometric signal which is detected (see FIG. 26).

This DNA conjugate, labeled E0030, was tested for enzyme activity and protein concentration using the Bradford method. The results are indicated in the table below.

| | |
|---|---|
| Protein concentration (ug/mL) | 186.7 |
| Enzyme Specific Activity (U/mg) | 984.4 |

Detection Antibody Processing:

This section describes the synthesis of the Antibody synthetic oligonucleotide conjugate.

Synthetic Oligonucleotide Processing:

As described above, the synthetic oligonucleotide is treated with a mercaptan to generate a free sulfhydryl group.

Approximately 50,000 pmols of A synthetic oligonucleotide is resuspended in autoclaved deionized water. Then 10 µL of 1×PBSE (136 mM NaCl, 2.7 mM KCl, 10.1 mM $Na_2HPO_4$, 1.8 mM $KH_2PO_4$, 5 mM EDTA, pH 7.4) and 20 µL of 1M DTT in autoclaved deionized water is added. The reaction is allowed to proceed for 15 minutes at room temperature. Once this reaction has completed, 20 µL of 1×PBSE is added, and the entire reaction is loaded onto a size exclusion column.

As described above, the DTT is removed from the synthetic oligonucleotide by size exclusion chromatography to prevent a reduction of the protein molecule.

A P-6 (Bio-Rad) size exclusion column is prepared using a 5 mL plastic pipette cut off at the '0' (mL) mark, silanized glass wool is placed into the tip of the pipette and the P-6 slurry pre-swelled in autoclaved deionized water is added until the column resin fills to the '1' (mL) mark. The column is rinsed with 5 mL of autoclaved deionized water. To this column the DTT treated synthetic oligonucleotide is loaded. Fourteen 200 µL fractions were collected in separate microcentrifuge tubes using the water as buffer. The fractions containing synthetic oligonucleotide were determined by the characteristic yellow color. Additionally, 1 µL samples were taken from each fraction and spotted onto saran wrap placed on top of a UV transilluminator. The brightly fluorescing spots contained synthetic oligonucleotide.

The fractions containing fluorescing material were combined and dried in a vacuum centrifuge at 60° C.

PEP-3 F(ab')2 Processing:

PEP-3 F(ab')2 was prepared by Pepsin cleavage of R&D Systems, Inc. Goat Anti-TNI peptide 3 Antibody Catalog number G-129-C using standard procedures well known to those skilled in the art. One mg of this protein in approximately 200 µL was reacted with 10 µL of 20 mM LC-SPDP at room temperature with mixing for 1.5 hours. The sample was then loaded and processed on an S-300 column as previously described.

Figure 27:
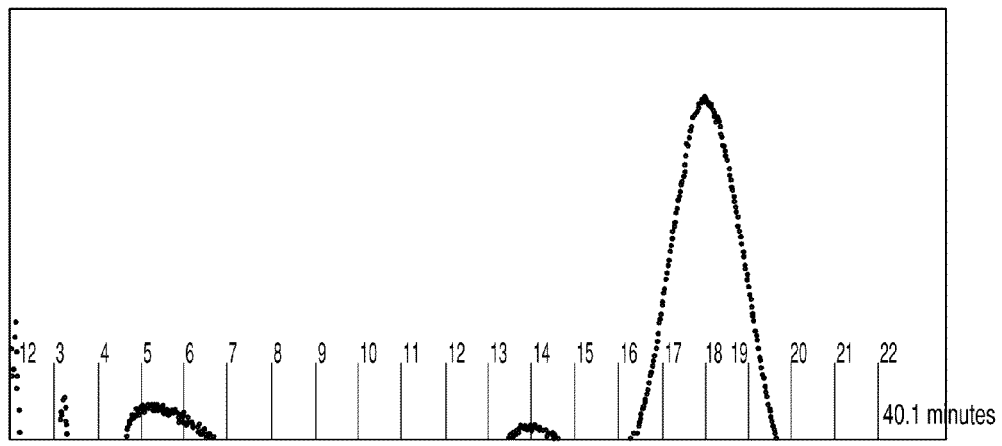
FIG. 27: S300 Column fractions from PEP-3 F(ab')2 reacted with LC-SPDP.

Fractions 16 to 19 (FIG. 27) were combined and concentrated by diafiltration as described above to about 500 µL final volume. The concentrated LC-SPDP activated PEP-3 F(ab')2 was added directly to the dried mercaptan treated thiol A synthetic oligonucleotide. The solution was gently pipetted to assure dissolution of the dried synthetic oligonucleotide. The reaction was incubated at 4° C. overnight with shaking. This material was purified on an S-300 column as previously described (FIG. 28).

The fractions were checked by determining UV fluorescence (by placing tubes over the UV transilluminator). Fractions 18 to 21 (FIG. 28) were combined and concentrated by diafiltration as described above. This antibody DNA conjugate, labeled as E0031, was tested for protein concentration using the Bradford method, which was determined to have a protein concentration of 54.5 ug/mL. The yellow color and UV fluorescence of this protein sample confirmed the attachment of the synthetic oligonucleotide.

Analyte Detection with DNA Based Conjugates:

Performed Antibody competition Assay by using standard cTnI cartridges and using MWC cTnI analyte samples either with or without conjugate samples. The reduction in signal is an indication that the analyte is bound by the F(ab) molecule of the DNA conjugate or the standard conjugate containing a F(ab) molecule. The above generated DNA-conjugate decreased signal and is suspected to have analyte binding ability as observed in FIG. 29.

Testing Analyte Binding Capability:

Analyte Detection with DNA Based Conjugates:

Four µL of PEP-3 F(ab')2-A [E0031] added to 4 µL ALP-A' [E0030] conjugate and 51.9 pg of cTnI MWC (manufacturer's working calibrator) were added to 16 µL of plasma and tested in a conjugate free 'immuno' i-STAT cartridge (a standard cTnI cartridge containing bead attached capture antibodies, electrogenic substrate, but no cTnI detection conjugate, this capability is supplied by the newly synthesized conjugate described above). Control with no MWC was also performed.

Figure 30:
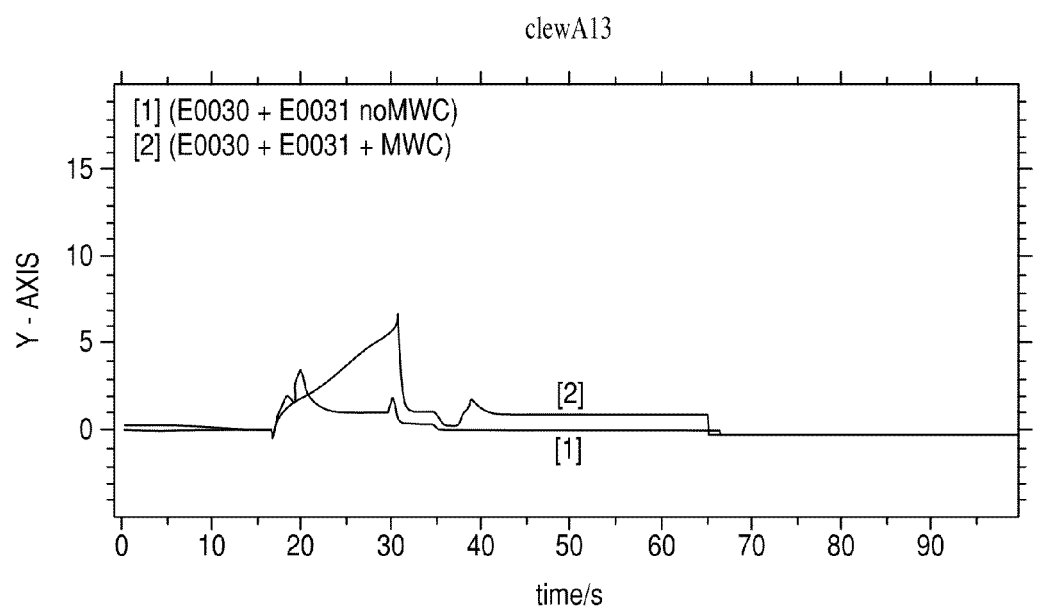
FIG. 30: Chronoamperometric results from i-STAT immuno-cartridge with cTnI capture beads and no conjugate, spiked with E0030 [747 ng]+E0031 [218 ng] with [2] analyte and without [1] MWC analyte.

FIG. 30 suggests that the dual conjugates described in FIG. 5 (ALP-A'+Antibody-A) bind to the capture beads to generate a small signal. The reference bead did not generate significant signal for either sample.

EXAMPLE 2

A second example of the invention is an enzyme-linked immunoassay (ELISA) based on synthetic oligonucleotides to bridge the detection antibody and ALP enzyme as a polymeric conjugate for analyte as shown in FIG. 6. In this example, a signal conjugate is generated with a repeating complementary DNA sequence attached to the antibody which then hybridizes with multiple ALP-synthetic oligonucleotide conjugates that increase the possible signal generation at the capture site when analyte is present. The repeating complementary DNA sequence is generated by creating a circular piece of synthetic DNA, followed by the generation of complementary multimer DNA of this sequence using a 5'-thiol containing synthetic oligonucleotide as a primer sequence and using Phi29 DNA polymerase which is used in rolling circle amplification. The specific DNA sequence is then conjugated to an antibody molecule, followed by hybridization with ALP molecules conjugated with complementary synthetic oligonucleotides.

The generation of the photopatterned metal, capture antibody conjugation to beads, cartridge design and assembly and microdispensing are previously described above.

Synthetic Oligonucleotide Sequences

A (DE)
(SEQ ID NO: 3)
5'- - thiol modifier C6 S-S-(T)20-TGATCGCTACGGTGGTATTGT-3'

A' (AP)
(SEQ ID NO: 2)
5'-thiol modifier C6 S-S-(T)20-ACAATACCACCGTAGCGATC*A-3' 6FAM X
(SEQ ID NO: 4)
5'-pACAATACCACCGTAGCGATCAAGTTATGCAACGCGGGAGTTGTGTATGAAGT-3'

*denotes phosphorothioate linkage
(T)20 denotes 20 'T' residues
p denotes phosphorylated 5'

Generation of ALP-A' DNA protein Conjugate

The same process as described in Example 1 for generating the ALP-A' DNA protein conjugate is used for Example 2. This conjugate is labeled E0030.

Generation of PEP-3 F(Ab')2 DNA Protein Conjugate

Constructing Synthetic Oligonucleotide Circles:

100,000 pmols of synthetic oligonucleotide X is incubated in 0.05M MOPS (2-(N-Morpholino)propanesulfonic acid), pH 7.5, 0.01 M KCL, 5 mM MgCl$_2$, 1.0 mM DTT, 0.05 mM ATP, 2.5 mM MnCl$_2$ with 20,000 units of Circlase ssDNA Ligase (Epicentre). The reaction is allowed to proceed at 60° C. overnight. An aliquot of this material is placed at 4° C. for later gel analysis. The processed synthetic oligonucleotides are then processed with 10,000 units of each Exonuclease I and Exonuclease III for 45 minutes at 37° C., followed by inactivation by heating at 90° C. for 10 minutes. The processed oligonucleotides are then purified by size exclusion chromatography using a P-6 resin (BioRad), as described above. The processed oligonucleotides are then confirmed to be circular by gel electrophoresis on a 20% acrylamide/7M urea denaturing gel. The change in electrophoretic migration compared to un-treated synthetic oligonucleotide confirms the circularization.

An amount of 50,000 pmol of synthetic oligonucleotide A is added to the prepared synthetic oligonucleotide X circles in 1×PBSE. The mixture is heated to 65° C. and allowed to slow cool to room temperature over 1 hour in a beaker with 100 mL of water. This efficiently anneals the thiol containing synthetic oligonucleotide with a free 3'-hydroxyl to the above prepared circular DNA structures.

The annealed reaction is added to a buffer containing a final concentration of 40 mM Tris-HCl, pH 7.5, 50 mM KCl, 10 mM MgCl$_2$, 5 mM (NH$_4$)$_2$SO$_4$, 4 mM DTT and 2000 units of RepliPHI Phi29 DNA Polymerase with 40 nmols each dATP, dCTP, dGTP, and dTTP. This extends the thiol containing synthetic oligonucleotide at the 3'-hydroxyl to generate a defined complementary multimer based on the circular template. Each of these multimers contains a 5'-thiol and the repeating complementary sequence of the circular DNA and is referred to as "tailed synthetic oligonucleotide."

Tailed Synthetic Oligonucleotide Processing:

For the protein-DNA conjugation the thiol modified portion of the tailed synthetic oligonucleotide is treated with a mercaptan (DTT) to generate a free sulfhydryl group which can subsequently react with the 2-pyridyldithio group of LC-SPDP (succinimidyl 6-[3'-(2-pyridyldithio)-propionamido) hexanoate crosslinker attached to the protein's amine group via its N-hydroxysuccinimide (NHS) ester group.

It should be noted that this procedure is typically performed in as short a period of time, as possible. Approximately 50,000 pmols of tailed A' synthetic oligonucleotide is resuspended in 10 μL of 1×PBSE (136 mM NaCl, 2.7 mM KCl, 10.1 mM Na$_2$HPO$_4$, 1.8 mM KH$_2$PO$_4$, 5 mM EDTA, pH 7.4) and 20 μL of 1M DTT (dithiothreitol) in autoclaved deionized water is added. The reaction is allowed to proceed for 15 minutes at room temperature. Once this reaction is complete, 50 μL of 1×PBSE is added, and the entire reaction is loaded onto a size exclusion column.

As the unreacted DTT will interfere with subsequent steps, it is removed using size exclusion chromatography.

A P-100 (Bio-Rad) size exclusion column is prepared using a 5 mL plastic pipette cut off at the '0' (mL) mark, siliconized glass wool is placed into the tip of the pipette and the P-100 slurry pre-swelled in autoclaved deionized water is added until the column resin fills to the '1' (mL) mark. The column is rinsed with 5 mL of autoclaved deionized water. To this column the DTT treated synthetic oligonucleotide is loaded. Fourteen 200 μL fractions were collected in separate microcentrifuge tubes using the water as buffer. Samples with absorbance at 260 nm were combined, as DNA has an absorbance at this wavelength. The DNA absorbing fractions were combined and dried in a vacuum centrifuge at 60° C.

PEP-3 F(ab')2 Processing:

PEP-3 F(ab')2 was prepared by Pepsin cleavage of R&D Systems, Inc. Goat Anti-TNI peptide 3 Antibody Catalog number G-129-C using standard procedures. One mg of this protein in approximately 200 μL was reacted with 10 μL of 20 mM LC-SPDP at room temperature with mixing for 1.5 hours. The sample was then loaded, and processed on an S-300 column as previously described.

Fractions containing the largest absorbing peak were combined and concentrated by diafiltration as described above to about 500 μL final volume. The concentrated LC-SPDP activated PEP-3 F(ab')2 was added directly to the dried mercaptan treated thiol A tailed synthetic oligonucleotide. The solution was gently pipetted to assure dissolution of the dried DNA. The reaction was incubated at 4° C. overnight with shaking. This material was purified on an S-300 column as previously described.

Analyte Detection with DNA Based Conjugates:

Four μL of PEP-3 F(ab')2-tailed oligonucleotide added to 4 μL ALP-A' [E0030] conjugate and 51.9 pg of cTnI MWC (manufacturer's working calibrator) were added to 16 of plasma and tested in a conjugate free 'immuno' i-STAT cartridge (a standard cTnI cartridge containing bead attached capture antibodies, electrogenic substrate, but no cTnI detection conjugate, this capability is supplied by the newly synthesized conjugate described above). Control with no MWC was also performed.

EXAMPLE 3

Another example of the invention is an enzyme-linked immunoassay (ELISA) based on synthetic oligonucleotides to bridge the detection antibody and ALP enzyme as a polymeric conjugate for analyte as shown in FIG. 6. In this example, a conjugate is generated with a repeating complementary DNA sequence attached to the antibody which then hybridizes with multiple ALP-synthetic oligonucleotide conjugates that increase the possible signal generation at the capture site when analyte is present. The repeating complementary DNA sequence is generated by cloning synthetic oligonucleotides into a phagemid, isolating single stranded DNA by techniques well known by those skilled in the art, followed by the generation of complementary multimer DNA of this sequence using a 5'-thiol containing synthetic oligonucleotide as a primer sequence and using T4 DNA polymerase (or any other DNA polymerase with a strand displacement capability). The specific DNA sequence is then conjugated to an antibody molecule, followed by hybridization with ALP molecules conjugated with complementary synthetic oligonucleotides.

The generation of the photopatterned metal, capture antibody conjugation to beads, cartridge design and assembly and microdispensing are previously described above.

Synthetic Oligonucleotide Sequences

```
A (DE)
                                           (SEQ ID NO: 3)
5'- - thiol modifier C6 S-S- (T)20-TGATCGCTACGGTGGTATTGT-3'

A' (AP)
                                           (SEQ ID NO: 2)
5'-thiol modifier C6 S-S-(T)20-ACAATACCACCGTAGCGATC*A-3'6FAM Y
                                           (SEQ ID NO: 5)
5'-AATTACAATACCACCGTAGCGATCACTACT-3'

Y'
                                           (SEQ ID NO: 6)
5'-AGCTAGTAGTGATCGCTACGGTGGTATTGT-3'

*denotes phosphorothioate linkage
(T)20 denotes 20 'T' residues
p denotes phosphorylated 5'
```

Generation of ALP-A' DNA Protein Conjugate

The same process as described in Example 1 for generating the ALP-A' DNA protein conjugate is used for Example 3. This conjugate is labeled E0030.

Cloning and Generation of Single Stranded Circular DNA Template

DNA Plasmids will be exploited to generate circular DNA fragments that can have specific DNA fragments cloned into them. Phagemid plasmids containing an fl origin of replication can be converted into single stranded DNA using a helper phage. This single stranded DNA can be easily scaled up, isolated and purified. All protocols are well known to those skilled in the art and based on protocols found in Sambrook and Russell (2001, Molecular Cloning: A Laboratory Manual, Third Edition, Cold Spring Harbour Laboratory Press, Cold Spring Harbour, N.Y.) This material can then be subsequently used to generate the tailed DNA fragments used in the ELISA assay using a strand displacing DNA polymerase like Phi29 or T4 DNA polymerase.

Ten ug of plasmid pGEM 11Zf+ (Promega Corp, Genbank sequence info: X65313) was restriction digested with 100 U each of R.EcoRI and R.HindIII restriction enzymes (New England Biolabs) using NEBuffer 2 for 1 hour at 37° C. The restricted DNA was then treated with 100 U of Antarctic Phosphatase (NEB) at 37° C. for 1 hour followed by heat inactivation at 65° C. for 5 minutes. This material was gel purified using a low melting point agarose gel, followed by agarose removal using beta-agarase (New England Biolabs) using the manufacturers protocol for ethanol precipitation of DNA. The DNA was dried in vacuo at 60° C., then resuspended in 20 uL of water.

100 pmol of synthetic oligonucleotides Y and Y' are combined and allowed to hybridize in TE buffer (10 mM Tris, pH 7.6, 0.1 mM EDTA) by first heating to 65° C. and slow cooling in 100 mL of water to room temperature for about 1 hour. The hybridized synthetic oligonucleotides are then added to the restricted plasmid prepared above. The DNA is ligated using 100 U of T4 DNA Ligase overnight at 14° C. And the ligation contained 20 units each of R.EcoRI and R.HindIII. To reduce the background of uncleaved material, the ligated mixture is then restriction digested with R.BamHI (New England Biolabs) for 1 hour at 37° C. following the manufacturer's instructions. The reaction is phenol/ether extracted, then concentrated by ethanol precipitation, followed by gel purification as described above.

Figure 31:
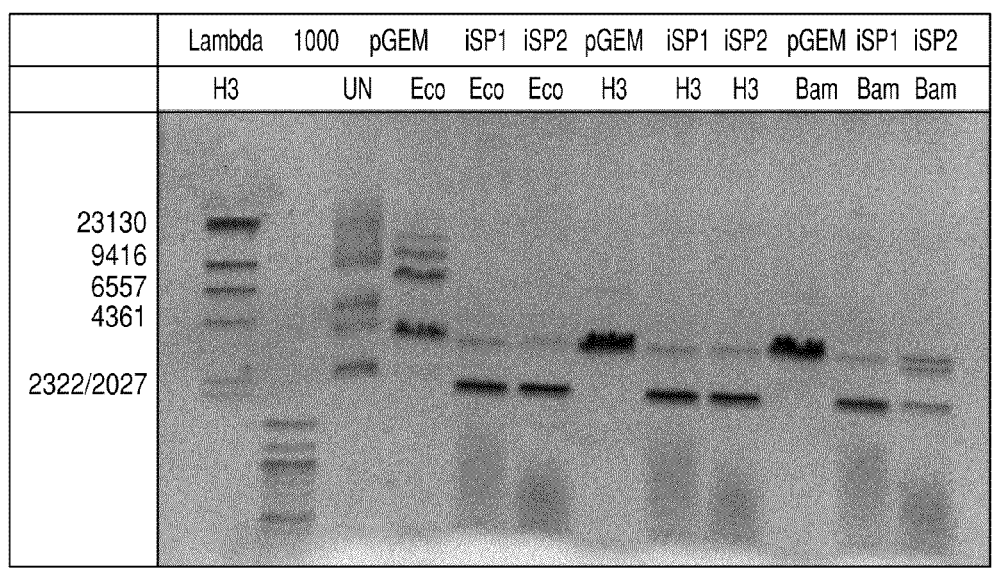
FIG. 31: Restriction Digestion of Putative Clones.

The purified DNA is then transformed into competent Invitrogen Top10F' competent bacterial cells (Invitrogen) according to the protocol of Hanahan et al. (1991, "Plasmid Transformation of *Escherichia coli* and other bacteria", Methods in Enzymology, vol 204: 63-113). These cells are competent for the take up of DNA. These cells contain a deletion in the complementary lacZ gene, are sensitive to amplicillin, tetracycline and kanamycin, contain the male F'-episome which is selectable with tetracycline and which permits the generation of single stranded DNA with the phagemid, contains the lacIq repressor which can be tightly de-repressed with IPTG and endA1 for reduced endonuclease activity. The transformed material is plated onto 2×YT media plates with 10 ug/mL ampicillin and grown overnight at 37 C. 12 single colonies were selected and grown in 5 mL 2×YT broth with 100 ug/mL ampicillin overnight at 37° C. Plasmid DNA was prepared using a rapid plasmid preparation (Birnboim & Doly, 1979, Nucleic Acids Research, vol 7(6):1513-1523). The DNA was resuspended in 20 uL water. 5 uL of each colony DNA preparation was restriction digested with 10 units R.BamHI at 37° C. for about 2 hours. The restriction digested DNA was electrophoresed on a 0.5% agarose gel (1×TBE). DNA observed to be uncleaved by R.BamHI, and with an obvious covalently closed circular (CCC) DNA band were selected for DNA sequencing (FIG. 31). These clones were sequenced using the M13 forward primer (SEQ ID NO. 7).

Single stranded DNA from the putative clones and an untreated phagemid clone are prepared from cells grown in 5 ml 2×YT broth with 60 ug/mL ampicillin and M13K07 help bacteriophage with 25 ug/mL kanamycin using the protocol of Sambrook & Russell (above). These single stranded preps are screened using an alpha-32P radiolabelled probe made from Terminal deoxynucleotidyl transferase labeled synthetic oligonucleotide A using a dot blot approach.

Two of the positive clones from the dot blot analysis are scaled up to 10×500 mL and single stranded DNA is prepared from these broths, as described above, generating about 1 mg of single stranded template DNA.

Generation of PEP-3 F(Ab')2 DNA Protein Conjugate

An amount of 5,000 pmol of synthetic oligonucleotide A is added to the prepared single stranded DNA template in 1×PBSE. The mixture is heated to 65° C. and allowed to slowly cool to room temperature over 1 hour in a beaker with 100 mL of water. This efficiently anneals the thiol containing synthetic oligonucleotide with a free 3'-hydroxyl to the above prepared circular DNA structures.

The annealed reaction is added to a buffer containing a final concentration of 40 mM Tris-HCL, pH 7.5, 50 mM KCl, 10 mM MgCl$_2$, 5 mM (NH$_4$)$_2$SO$_4$, 4 mM DTT and 2000 units of RepliPHI Phi29 DNA Polymerase with 40 nmols each dATP, dCTP, dGTP, and dTTP. This extends the thiol containing synthetic oligonucleotide at the 3'-hydroxyl to generate a defined complementary multimer based on the circular template. Each of these multimers contains a 5'-thiol and the repeating complementary sequence of the circular DNA and is referred to as "tailed synthetic oligonucleotide."

Tailed Synthetic Oligonucleotide Processing:

For the protein-DNA conjugation the thiol modified portion of the tailed synthetic oligonucleotide is treated with a mercaptan (DTT) to generate a free sulthydryl group which can subsequently react with the 2-pyridyldithio group of LC-SPDP (succinimidyl 6-[3'-(2-pyridyldithio)-propionamido) hexanoate crosslinker attached to the protein's amine group via its N-hydroxysuccinimide (NHS) ester group.

It should be noted that this procedure is typically performed in as short a period of time, as possible. Approximately 5,000 pmols of tailed A' synthetic oligonucleotide is resuspended in 10 μL of 1×PBSE (136 mM NaCl, 2.7 mM KCl, 10.1 mM Na$_2$HPO$_4$, 1.8 mM KH$_2$PO$_4$, 5 mM EDTA, pH 7.4) and 20 μL of 1M DTT (dithiothreitol) in autoclaved deionized water is added. The reaction is allowed to proceed for 15 minutes at room temperature. Once this reaction is complete, 50 μL of 1×PBSE is added, and the entire reaction is loaded onto a size exclusion column.

As the unreacted DTT will interfere with subsequent steps, it is removed using size exclusion chromatography.

A P-100 (Bio-Rad) size exclusion column is prepared using a 5 mL plastic pipette cut off at the '0' (mL) mark, siliconized glass wool is placed into the tip of the pipette and the P-100 slurry pre-swelled in autoclaved deionized water is added until the column resin fills to the 1' (mL) mark. The column is rinsed with 5 mL of autoclaved deionized water. To this column the DTT treated synthetic oligonucleotide is loaded. Fourteen 200 μL fractions were collected in separate microcentrifuge tubes using the water as buffer. Samples with absorbance at 260 nm were combined, as DNA has an absorbance at this wavelength. The DNA absorbing fractions were combined and dried in a vacuum centrifuge at 60° C.

PEP-3 F(ab')2 Processing:

PEP-3 F(ab')2 was prepared by Pepsin cleavage of R&D Systems, Inc. Goat Anti-TNI peptide 3 Antibody Catalog number G-129-C using standard procedures. One hundred ug of this protein in approximately 200 μL was reacted with 10 μL of 20 mM LC-SPDP at room temperature with mixing for 1.5 hours. The sample was then loaded and processed on an S-300 column as previously described.

Fractions containing the largest absorbing peak were combined and concentrated by diafiltration as described above to about 500 μL final volume. The concentrated LC-SPDP activated PEP-3 F(ab')2 was added directly to the dried mercaptan treated thiol A tailed DNA. The solution was gently pipetted to assure dissolution of the dried DNA. The reaction was incubated at 4° C. overnight with shaking. This material was purified on an S-300 column as previously described.

Analyte Detection with DNA Based Conjugates:

Four μL of PEP-3 F(ab')2-A tailed DNA added to 4 μL ALP-A' [E0030] conjugate and 51.9 pg of cTnI MWC (manufacturer's working calibrator) were added to 16 μL of plasma and tested in a conjugate free 'immuno' i-STAT cartridge (a standard cTnI cartridge containing bead attached capture antibodies, electrogenic substrate, but no cTnI detection conjugate, this capability is supplied by the newly synthesized conjugate described above). Control with no MWC was also performed.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments. All publications, patents and patent applications referred to herein are incorporated by reference in their entirety to the same extent as if each individual publication, patent or patent application was specifically and individually indicated to be incorporated by reference in its entirety.

What is claimed is:

1. A single-use cartridge for performing an immunoassay, comprising:
   a sample entry port for receiving a blood sample suspected of containing a target analyte,
   a conduit containing an electrode,
   a region containing a wash fluid,
   a waste chamber,
   immobilized first antibody capable of binding to said target analyte,
   second antibody disposed in a solubilizing agent disposed within said conduit and capable of binding to said target analyte, wherein the second antibody is attached to a first single stranded nucleotide, and
   one or more signal elements each attached to a second single stranded nucleotide having complimentary base pairs to the first single stranded nucleotide;
   wherein:
   the wash fluid is capable of washing said blood sample from said electrode in said conduit into said waste chamber, and
   a 3'-end or 5'-end of the a first single stranded nucleotide and the a second single stranded nucleotide is protected from endogenous exonuclease activity from said blood sample within the conduit by incorporating a protective chemical group.

2. The cartridge of claim 1, wherein the one or more signal elements comprise a non-enzymatic detection moiety that is selected from the group consisting of fluorescent, colorimetric, and radioactive elements.

3. The cartridge of claim 1, wherein the one or more signal elements comprise one or more signal enzymes, the cartridge further comprising:
   a region containing an enzyme substrate,
   wherein said enzyme substrate is capable of reacting with said one or more signal enzymes to generate a signal at said electrode proportionate to the amount of said target analyte in said blood sample.

4. The cartridge of claim 3, wherein the first antibody binds to a first epitope of the target analyte.

5. The cartridge of claim 3, wherein the second antibody binds to a second epitope of the target analyte.

6. The cartridge of claim 3, wherein the one or more signal enzymes are selected from the group consisting of alkaline phosphatase, glucose oxidase, lactate oxidase, urease, horseradish peroxidase, galactose oxidase, and beta-galactosidase.

* * * * *

SEQUENCE LISTING

```
<160> NUMBER OF SEQ ID NOS: 7

<210> SEQ ID NO 1
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: amino C12 modifier at 5' end
```

<400> SEQUENCE: 1
tttttttttt tttttttttt tgatcgctac ggtggtattg t            41

<210> SEQ ID NO 2
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: thiol modifier C6 S-S at 5' end
<220> FEATURE:
<221> NAME/KEY: misc_feature
<222> LOCATION: (40)..(41)
<223> OTHER INFORMATION: phosphorothioate linkage

<400> SEQUENCE: 2
tttttttttt tttttttttt acaataccac cgtagcgatc a            41

<210> SEQ ID NO 3
<211> LENGTH: 41
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: thiol modifier C6 S-S at 5' end

<400> SEQUENCE: 3
tttttttttt tttttttttt tgatcgctac ggtggtattg t            41

<210> SEQ ID NO 4
<211> LENGTH: 52
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: phosphorylated 5' end

<400> SEQUENCE: 4
acaataccac cgtagcgatc aagttatgca acgcgggagt tgtgtatgaa gt            52

<210> SEQ ID NO 5
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 5
aattacaata ccaccgtagc gatcactact            30

<210> SEQ ID NO 6
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 6

```
agctagtagt gatcgctacg gtggtattgt                                      30

<210> SEQ ID NO 7
<211> LENGTH: 225
<212> TYPE: DNA
<213> ORGANISM: Artificial Sequence
<220> FEATURE:
<223> OTHER INFORMATION: Synthetic oligonucleotide

<400> SEQUENCE: 7
tgtatacgac tcactatagg gcgaattggc caagtcggcc gagctcgaat tacaatacca     60
ccgtagcgat cactactagc ttgagtattc tatagtgtca cctaaatagc ttggcgtaat   120
catggtcata gctgtttcct gtgtgaaatt gttatccgct cacaattcca cacaacatac   180
gagccggaag cataaagtgt aaagcctggg gtgcctaatg agtga                   225
```